(12) United States Patent
Abe et al.

(10) Patent No.: US 9,608,287 B2
(45) Date of Patent: *Mar. 28, 2017

(54) NON-AQUEOUS ELECTROLYTIC SOLUTION, ELECTRICAL STORAGE DEVICE UTILIZING SAME, AND CYCLIC SULFONIC ACID ESTER COMPOUND

(75) Inventors: Koji Abe, Yamaguchi (JP); Shoji Shikita, Yamaguchi (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 300 days.

This patent is subject to a terminal disclaimer.

(21) Appl. No.: 14/113,722

(22) PCT Filed: Apr. 25, 2012

(86) PCT No.: PCT/JP2012/061142
§ 371 (c)(1),
(2), (4) Date: Dec. 11, 2013

(87) PCT Pub. No.: WO2012/147818
PCT Pub. Date: Nov. 1, 2012

(65) Prior Publication Data
US 2014/0093787 A1   Apr. 3, 2014

(30) Foreign Application Priority Data

Apr. 26, 2011 (JP) ................. 2011-098290
Jul. 20, 2011 (JP) .................. 2011-159035
Oct. 14, 2011 (JP) ................. 2011-227338

(51) Int. Cl.
*H01M 10/056* (2010.01)
*C07D 327/04* (2006.01)
(Continued)

(52) U.S. Cl.
CPC ........ *H01M 10/056* (2013.01); *C07D 327/04* (2013.01); *C07D 327/06* (2013.01);
(Continued)

(58) Field of Classification Search
CPC ........... H01M 10/056; H01M 10/0525; H01M 10/0567; C07D 327/04; C07D 327/06; Y02T 10/7011
See application file for complete search history.

(56) References Cited

U.S. PATENT DOCUMENTS 9,318,776 B2 * 4/2016 Abe ................. H01M 10/0525
2006/0124973 A1 * 6/2006 Arai et al. .................... 257/223
(Continued)

FOREIGN PATENT DOCUMENTS

CN           1277468 A    12/2000
CN           1880388 A    12/2006
(Continued)

OTHER PUBLICATIONS

Archiv der Pharmazie (1985), 318(4), 304-11 ( CAS Abstract).*
Archiv der Pharmazie (1985), 318(4), 304-11.*
JP 2008218298 Abstract.*
CN 101202364 MT.*
Journal of the Electrochemical Society, 161 (6) A863-A870 (2014).*
CN 102074738 MT.*
(Continued)

*Primary Examiner* — Alex Usyatinsky
(74) *Attorney, Agent, or Firm* — Oblon, McClelland, Maier & Neustadt, L.L.P.

(57) ABSTRACT

An object of the present invention is to provide a nonaqueous electrolytic solution capable of improving electrochemical characteristics in a broad temperature range, an energy storage device using it.

A nonaqueous electrolytic solution of an electrolyte salt dissolved in a nonaqueous solvent, which comprises at least one cyclic sulfonic acid ester compound represented by the following general formula (I), and an energy storage device.

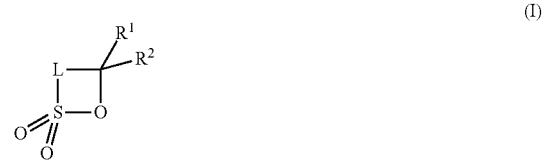

(wherein $R^1$ and $R^2$ may be the same or different, each representing a hydrogen atom, an alkyl group in which at least one hydrogen atom may be substituted with a halogen atom, or a halogen atom; L represents a divalent hydrocarbon group of an alkylene group in which at least one hydrogen atom is substituted with $OR^3$, or a divalent hydrocarbon group of an alkylene group in which at least one methylene ($CH_2$) is substituted with $C(=O)$; $R^3$ represents a formyl group, an alkylcarbonyl group, an alkenylcarbonyl group, an alkynylcarbonyl group, an arylcarbonyl group, an alkoxycarbonyl group, an alkenyloxycarbonyl group, an alkynyloxycarbonyl group, an aryloxycarbonyl group, a 2,2-dioxide-1,2-oxathiolan-4-yloxycarbonyl group, a 2,2-dioxide-1,2-oxathian-4-yloxycarbonyl group, an alkanesulfonyl group, an arylsulfonyl group, a dialkylphosphoryl group, an alkoxy(alkyl)phosphoryl group, a dialkoxyphosphoryl group, $-S(O)-OR^4$, or $-C(O)CH_2P(O)(OR^5)_2$; $R^4$ represents an alkyl group, a 2,2-dioxide-1,2-oxathiolan-4-yl group, or a 2,2-dioxide-1,2-oxathian-4-yl group; $R^5$ represents an alkyl group; further, in $R^3$, at least one hydrogen atom may be substituted with a halogen atom, and L may be further substituted with any of an alkyl group, a haloalkyl group or a halogen atom).

18 Claims, No Drawings

(51) Int. Cl.
*C07D 327/06* (2006.01)
*H01M 10/0567* (2010.01)
*H01M 10/0525* (2010.01)

(52) U.S. Cl.
CPC .... *H01M 10/0567* (2013.01); *H01M 10/0525* (2013.01); *Y02T 10/7011* (2013.01)

(56) References Cited

U.S. PATENT DOCUMENTS

| | | | |
|---|---|---|---|
| 2007/0059606 | A1 | 3/2007 | Lee et al. |
| 2007/0231707 | A1* | 10/2007 | Abe ................. H01M 10/0525 429/340 |
| 2008/0286648 | A1* | 11/2008 | Ihara ................. H01M 10/0567 429/188 |
| 2011/0123871 | A1* | 5/2011 | Nakagawa et al. ........... 429/326 |
| 2012/0130089 | A1* | 5/2012 | Kuramoto ............ C07D 327/10 549/34 |
| 2015/0221985 | A1* | 8/2015 | Abe ...................... H01G 11/60 429/329 |
| 2015/0333370 | A1* | 11/2015 | Abe ................. H01M 10/0567 429/332 |

FOREIGN PATENT DOCUMENTS

| | | | | |
|---|---|---|---|---|
| CN | 101202364 | * | 6/2008 | ............ H01M 10/05 |
| CN | 101202364 A | | 6/2008 | |
| CN | 102074738 | * | 5/2011 | .......... H01M 10/058 |
| JP | 2002 329528 | | 11/2002 | |
| JP | 2006 004813 | | 1/2006 | |
| JP | 2007 112737 | | 5/2007 | |
| JP | 2008 147119 | | 6/2008 | |
| JP | 2008218298 | * | 9/2008 | ............ H01M 10/36 |
| JP | 2011 184390 | | 9/2011 | |
| WO | 2005 117197 | | 12/2005 | |
| WO | WO/2009/107786 | * | 9/2009 | |
| WO | 2011 016440 | | 2/2011 | |

OTHER PUBLICATIONS

The Extended European Search Report issued Dec. 8, 2014, in Application No. / Patent No. 12776419.9-1360 / 2704246.
International Search Report Issued Jul. 24, 2012 in PCT/JP12/061142 Filed Apr. 25, 2012.
Combined Chinese Office Action and Search Report issued May 6, 2015 in Patent Application No. 201280020394.6.
Li Tian, "The Study on the Synthesis and Reaction Properties of 1,3-unsaturated sultone", Wanfang Data, Dec. 21, 2010, 3 pages.

* cited by examiner

NON-AQUEOUS ELECTROLYTIC SOLUTION, ELECTRICAL STORAGE DEVICE UTILIZING SAME, AND CYCLIC SULFONIC ACID ESTER COMPOUND

TECHNICAL FIELD

The present invention relates to a nonaqueous electrolytic solution capable of improving electrochemical characteristics in a broad temperature range, an energy storage device using it, and a cyclic sulfonic acid ester compound.

BACKGROUND ART

In recent years, energy storage devices, especially lithium secondary batteries have been widely used for small-sized electronic devices, such as mobile telephones, notebook-size personal computers and the like, for electric vehicles, as well as for electric power storage. These electronic devices and vehicles may be used in a broad temperature range, for example, at midsummer high temperatures or at frigid low temperatures, and are therefore required to be improved in point of electrochemical characteristics well balanced in a broad temperature range.

Especially for preventing global warming, it is imperative to reduce $CO_2$ emissions, and of environment-responsive vehicles with, as mounted thereon, an electrical storage installation that comprises an energy storage device, such as a lithium secondary battery, a capacitor or the like, early popularization of hybrid electric vehicles (HEV), plug-in hybrid electric vehicles (PHEV) and battery electric vehicles (BEV) is desired. Vehicles could take a long travel distance and therefore could be used in regions in a broad temperature range covering from extremely-hot tropical regions to frigid regions. In particular, therefore, it is desired that the electrochemical characteristics of in-car energy storage devices for those vehicles are not worsened even in use thereof in a broad temperature range covering from high temperatures to low temperatures.

In this specification, the term, lithium secondary battery is used as a concept including a so-called lithium ion secondary battery.

A lithium secondary battery is mainly constituted of a positive electrode and a negative electrode containing a material capable of absorbing and releasing lithium, and a nonaqueous electrolytic solution containing a lithium salt and a nonaqueous solvent. For the nonaqueous solvent, used are carbonates, such as ethylene carbonate (EC), propylene carbonate (PC), etc.

As the negative electrode, known are metal lithium, and metal compounds (metal elemental substances, oxides, alloys with lithium, etc.) and carbon materials capable of absorbing and releasing lithium. In particular, a lithium secondary battery using a carbon material capable of absorbing and releasing lithium, such as coke, artificial graphite, natural graphite or the like, has been widely put into practical use.

For example, it is known that, in a lithium secondary battery using a highly-crystalline carbon material, such as natural graphite, artificial graphite or the like as the negative electrode material therein, the decomposed products or gas generated through reductive decomposition of the solvent in the nonaqueous electrolytic solution on the surface of the negative electrode during charging detracts from the electrochemical reaction favorable for the battery, therefore worsening the cycle properties of the battery. Deposition of the decomposed products of the nonaqueous solvent interferes with smooth absorption and release of lithium by the negative electrode, and therefore the electrochemical characteristics of the battery in use thereof in a broad temperature range may often tend to worsen.

In addition, it is known that a lithium secondary battery using a lithium metal or its alloy, or a metal elemental substance, such as tin, silicon or the like or its metal oxide as the negative electrode material therein could have a high initial battery capacity but the battery capacity and the battery performance thereof, such as cycle properties may greatly worsen, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed products of the nonaqueous solvent may interfere with smooth absorption and release of lithium by the negative electrode, and therefore the electrochemical characteristics of the battery in use thereof in a broad temperature range may often tend to worsen.

On the other hand, it is known that, in a lithium secondary battery using, for example, $LiCoO_2$, $LiMn_2O_4$, $LiNiO_2$, $LiFePO_4$ or the like as the positive electrode, the nonaqueous solvent in the nonaqueous electrolytic solution locally undergoes partial oxidative decomposition in the interface between the positive electrode material and the nonaqueous electrolytic solution in the charged state and the decomposed products or the gas thereby generated as a result of the partial oxidative decomposition interferes with the electrochemical reaction favorable for the battery, and therefore the electrochemical characteristics of the battery would be thereby also worsened in use in a broad temperature range.

As in the above, the decomposed products and the gas generated through decomposition of the nonaqueous electrolytic solution on the positive electrode or the negative electrode may interfere with the movement of lithium ions or may swell the battery, and the battery performance is thereby worsened. Despite the situation, electronic appliances equipped with lithium secondary batteries therein are offering more and more an increasing range of functions and are being in a stream of further increase in power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the electrochemical characteristics of the battery in use thereof in a broad temperature range.

PTL 1 proposes a nonaqueous electrolytic solution containing a hydroxypropane sultone and suggests that the hydroxy group of the hydroxypropane sultone adsorbs to lithium metal before discharge and during charge and discharge to thereby form a dense and stable surface film on the negative electrode and the cycle properties are thereby improved.

CITATION LIST

Patent Literature

PTL 1: JP-A 2006-4813

SUMMARY OF INVENTION

Technical Problem

An object of the present invention is to provide a nonaqueous electrolytic solution capable of improving electrochemical characteristics in a broad temperature range, an energy storage device using it, and a cyclic sulfonic acid ester compound.

Solution to Problem

The present inventors have investigated in detail the performance of the nonaqueous electrolytic solutions in the above-mentioned prior art. As a result, in the nonaqueous electrolytic solution of the above-mentioned patent literature, the hydroxy group of the hydroxypropane sulfone is readily reduced, and therefore the nonaqueous electrolytic solution would be excessively decomposed during high-temperature storage in a charged state therefore causing self-discharge and increasing the resistance of the negative electrode, and in fact, therefore, the nonaqueous electrolytic solution could not exhibit a sufficient effect for the problem of improving the electrochemical characteristics of batteries in a broad temperature range, such as low-temperature discharge characteristics thereof after high-temperature storage, etc.

Given the situation, the present inventors have assiduously studied for the purpose of solving the above-mentioned problems, and have found that, when at least one specific cyclic sulfonic acid ester compound is added to a nonaqueous electrolytic solution of an electrolyte salt dissolved in a nonaqueous solvent, then the electrochemical characteristics of energy storage devices in a broad temperature range, especially the electrochemical characteristics of lithium batteries can be improved, and have completed the present invention.

Specifically, the present invention provides the following (1) to (3):

(1) A nonaqueous electrolytic solution of an electrolyte salt dissolved in a nonaqueous solvent, which comprises at least one cyclic sulfonic acid ester compound represented by the following general formula (I):

[Chem. 1]

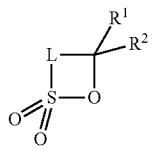

(I)

(In the formula, $R^1$ and $R^2$ may be the same or different, each representing a hydrogen atom, an alkyl group having from 1 to 6 carbon atoms in which at least one hydrogen atom may be substituted with a halogen atom, or a halogen atom; L represents a divalent hydrocarbon group of an alkylene group having 2 or 3 carbon atoms in which at least one hydrogen atom is substituted with $OR^3$, or a divalent hydrocarbon group of an alkylene group having 2 or 3 carbon atoms in which at least one methylene ($CH_2$) group is substituted with a group $C(=O)$; $R^3$ represents a formyl group, an alkylcarbonyl group having from 2 to 7 carbon atoms, an alkenylcarbonyl group having from 3 to 7 carbon atoms, an alkynylcarbonyl group having from 3 to 7 carbon atoms, an arylcarbonyl group having from 7 to 13 carbon atoms, an alkoxycarbonyl group having from 2 to 7 carbon atoms, an alkenyloxycarbonyl group having from 3 to 7 carbon atoms, an alkynyloxycarbonyl group having from 4 to 7 carbon atoms, an aryloxycarbonyl group having from 7 to 13 carbon atoms, a 2,2-dioxide-1,2-oxathiolan-4-yloxycarbonyl group, a 2,2-dioxide-1,2-oxathian-4-yloxycarbonyl group, an alkanesulfonyl group having from 1 to 6 carbon atoms, an arylsulfonyl group having from 6 to 12 carbon atoms, a dialkylphosphoryl group having from 2 to 12 carbon atoms, an alkoxy(alkyl)phosphoryl group having from 2 to 12 carbon atoms, a dialkoxyphosphoryl group having from 2 to 12 carbon atoms, a group —S(O)—$OR^4$ or a group —C(O)CH$_2$P(O)($OR^5$)$_2$; $R^4$ represents an alkyl group having from 1 to 6 carbon atoms, a 2,2-dioxide-1,2-oxathiolan-4-yl group, or a 2,2-dioxide-1,2-oxathian-4-yl group; $R^5$ represents an alkyl group having from 1 to 6 carbon atoms. Further, in $R^3$, at least one hydrogen atom may be substituted with a halogen atom, and L may be further substituted with any of an alkyl group having from 1 to 6 carbon atoms, a haloalkyl group having from 1 to 6 carbon atoms or a halogen atom.)

(2) An energy storage device comprising a positive electrode, a negative electrode, and a nonaqueous electrolytic solution of an electrolyte salt dissolved in a nonaqueous solvent, wherein the nonaqueous electrolytic solution is the nonaqueous electrolytic solution of the above (1).

(3) A cyclic sulfonic acid ester compound represented by the following general formula (II):

[Chem. 2]

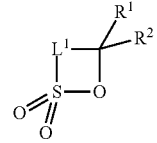

(II)

(In the formula, $R^1$ and $R^2$ may be the same or different, each representing a hydrogen atom, an alkyl group having from 1 to 6 carbon atoms in which at least one hydrogen atom may be substituted with a halogen atom, or a halogen atom; $L^1$ represents a divalent hydrocarbon group of an alkylene group having 2 or 3 carbon atoms in which at least one hydrogen atom is substituted with $OR^6$, or a divalent hydrocarbon group of an alkylene group having 2 or 3 carbon atoms in which at least one methylene ($CH_2$) group is substituted with a group $C(=O)$; $R^6$ represents a formyl group, an alkenylcarbonyl group having from 3 to 7 carbon atoms, an alkynylcarbonyl group having from 3 to 7 carbon atoms, an alkoxycarbonyl group having from 2 to 7 carbon atoms, an alkenyloxycarbonyl group having from 3 to 7 carbon atoms, an alkynyloxycarbonyl group having from 4 to 7 carbon atoms, an aryloxycarbonyl group having from 7 to 13 carbon atoms, a 2,2-dioxide-1,2-oxathiolan-4-yloxycarbonyl group, a 2,2-dioxide-1,2-oxathian-4-yloxycarbonyl group, a dialkylphosphoryl group having from 2 to 12 carbon atoms, an alkoxy(alkyl)phosphoryl group having from 2 to 12 carbon atoms, a dialkoxyphosphoryl group having from 2 to 12 carbon atoms, a group —S(O)—$OR^4$ or a group —C(O)CH$_2$P(O)($OR^5$)$_2$; $R^4$ represents an alkyl group having from 1 to 6 carbon atoms, a 2,2-dioxide-1,2-oxathiolan-4-yl group, or a 2,2-dioxide-1,2-oxathian-4-yl group; $R^5$ represents an alkyl group having from 1 to 6 carbon atoms. Further, in $R^6$, at least one hydrogen atom may be substituted with a halogen atom, and $L^1$ may be further substituted with any of an alkyl group having from 1 to 6 carbon atoms, a haloalkyl group having from 1 to 6 carbon atoms or a halogen atom. However, when $L^1$ is a divalent hydrocarbon group of an alkylene group having 2 or 3 carbon atoms in which at least one methylene ($CH_2$) group is substituted with a group (C=O), then $R^1$ and $R^2$ are hydrogen atoms.)

Advantageous Effects of Invention

According to the present invention, there are provided a nonaqueous electrolytic solution capable of improving the electrochemical characteristics of energy storage devices in a broad temperature range, especially the low-temperature discharge characteristics thereof after high-temperature storage, an energy storage device, such as lithium batteries and others using the nonaqueous electrolytic solution, and a specific cyclic sulfonic acid ester compound.

DESCRIPTION OF EMBODIMENTS

The present invention relates to a nonaqueous electrolytic solution, an energy storage device using it, and a specific cyclic sulfonic acid ester compound.
(Nonaqueous Electrolytic Solution)

The nonaqueous electrolytic solution of the present invention comprises an electrolyte salt dissolved in a nonaqueous solvent, and comprises at least one cyclic sulfonic acid ester compound represented by the above-mentioned general formula (I).

Though not always clear, the reason why the nonaqueous electrolytic solution of the present invention can remarkably improve the electrochemical characteristics of energy storage devices in a broad temperature range may be considered as follows:

The cyclic sulfonic acid ester compound represented by the above-mentioned general formula (I) in the present invention has, on the divalent linking group that links the carbon atom and the sulfur atom adjacent to the oxygen atom (—O—) of the sulfonyloxy group (—S(=O)$_2$—O—) therein, a specific electron attractive group of a group OC(=O)R, a group OC(=O)OR, a group OS(=O)$_2$R, a group OP(=O)(OR)(OR') a group OP(=O)(OR)R', a group OP(=O)RR' or a group C(=O). Accordingly, unlike a hydroxypropane sulfone that excessively decomposes through reductive decomposition of the hydroxy group therein, the ester compound does not excessively decompose to increase the resistance of a negative electrode. Moreover, when the ester compound decomposes on an electrode, it polymerizes through opening of the cyclic structure thereof to form a surface film having high heat resistance and, in addition, since the surface film contains a substituent of a group OC(=O)R, a group OC(=O)OR, a group OS(=O)$_2$ R, a group OP(=O)(OR)(OR'), a group OP(=O)(OR)R', a group OP(=O)RR', a group C(=O) or the like, the substituent therein could function a gentle trap site for lithium ions, and accordingly, the lithium ion conductivity of the surface film could remarkably improve to thereby bring about the effect of improving the electrochemical characteristics of batteries in a broad temperature range.

In addition, it has been found, when any other substituent, such as a methoxy group is introduced into the compound in place of the above-mentioned substituent therein, then there occur some problems in that the chemical stability of the compound is lowered and the compound may be readily decomposed; however, it has also been found that the cyclic sulfonic acid ester compound represented by the general formula (I) in the present invention is chemical stable.

The cyclic sulfonic acid ester compound to be contained in the nonaqueous electrolytic solution of the present invention is represented by the following general formula (I):

[Chem. 3]

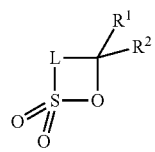

(I)

(In the formula, $R^1$ and $R^2$ may be the same or different, each representing a hydrogen atom, an alkyl group having from 1 to 6 carbon atoms in which at least one hydrogen atom may be substituted with a halogen atom, or a halogen atom; L represents a divalent hydrocarbon group of an alkylene group having 2 or 3 carbon atoms in which at least one hydrogen atom is substituted with $OR^3$, or a divalent hydrocarbon group of an alkylene group having 2 or 3 carbon atoms in which at least one methylene ($CH_2$) group is substituted with a group C(=O); $R^3$ represents a formyl group, an alkylcarbonyl group having from 2 to 7 carbon atoms, an alkenylcarbonyl group having from 3 to 7 carbon atoms, an alkynylcarbonyl group having from 3 to 7 carbon atoms, an arylcarbonyl group having from 7 to 13 carbon atoms, an alkoxycarbonyl group having from 2 to 7 carbon atoms, an alkenyloxycarbonyl group having from 3 to 7 carbon atoms, an alkynyloxycarbonyl group having from 4 to 7 carbon atoms, an aryloxycarbonyl group having from 7 to 13 carbon atoms, a 2,2-dioxide-1,2-oxathiolan-4-yloxycarbonyl group, a 2,2-dioxide-1,2-oxathian-4-yloxycarbonyl group, an alkanesulfonyl group having from 1 to 6 carbon atoms, an arylsulfonyl group having from 6 to 12 carbon atoms, a dialkylphosphoryl group having from 2 to 12 carbon atoms, an alkoxy(alkyl)phosphoryl group having from 2 to 12 carbon atoms, a dialkoxyphosphoryl group having from 2 to 12 carbon atoms, a group —S(O)—$OR^4$ or a group —C(O)$CH_2$P(O)($OR^5$)$_2$; $R^4$ represents an alkyl group having from 1 to 6 carbon atoms, a 2,2-dioxide-1,2-oxathiolan-4-yl group, or a 2,2-dioxide-1,2-oxathian-4-yl group; $R^5$ represents an alkyl group having from 1 to 6 carbon atoms. Further, in $R^3$, at least one hydrogen atom may be substituted with a halogen atom, and L may be further substituted with any of an alkyl group having from 1 to 6 carbon atoms, a haloalkyl group having from 1 to 6 carbon atoms or a halogen atom.)

In the above-mentioned general formula (I), $R^1$ and $R^2$ may be the same or different, each representing a hydrogen atom, an alkyl group having from 1 to 6 carbon atoms in which at least one hydrogen atom may be substituted with a halogen atom, or a halogen atom, and is preferably a hydrogen atom, an alkyl group having from 1 to 4 carbon atoms in which at least one hydrogen atom may be substituted with a halogen atom, or a halogen atom, more preferably a hydrogen atom, or an alkyl group having 1 or 2 carbon atoms in which at least one hydrogen atom may be substituted with a halogen atom.

As specific examples of $R^1$ and $R^2$, preferably mentioned are a hydrogen atom; a linear alkyl group, such as a methyl group, an ethyl group, an n-propyl group, an n-butyl group, an n-pentyl group, an n-hexyl group, etc.; a branched alkyl group, such as an isopropyl group, a sec-butyl group, a tart-butyl group, a tert-amyl group, etc.; a fluoroalkyl group, such as a fluoromethyl group, a difluoromethyl group, a trifluoromethyl group, a 2,2,2-trifluoroethyl group, etc.; and a fluorine atom. Above all, more preferred are a hydrogen atom, a methyl group, an ethyl group, an n-propyl group, a difluoromethyl group, a trifluoromethyl group, a 2,2,2-trifluoroethyl group; and even more preferred are a hydrogen atom and a methyl group.

L in the above-mentioned general formula (I) represents a divalent hydrocarbon group of an alkylene group having 2 or 3 carbon atoms in which at least one hydrogen atom is substituted with $OR^3$, or a divalent hydrocarbon group of an alkylene group having 2 or 3 carbon atoms in which at least one methylene ($CH_2$) group is substituted with a group C(=O); and the carbon number of the group is preferably 2.

$R^3$ is as defined above, and is preferably a formyl group, an alkylcarbonyl group having from 2 to 7 carbon atoms, an alkenylcarbonyl group having from 3 to 7 carbon atoms, an alkoxycarbonyl group having from 2 to 5 carbon atoms, an alkenyloxycarbonyl group having from 3 to 7 carbon atoms, or an alkynyloxycarbonyl group having from 4 to 7 carbon atoms, more preferably a formyl group, an alkylcarbonyl group having from 2 to 5 carbon atoms, an alkenylcarbonyl group having from 3 to 5 carbon atoms, an alkoxycarbonyl group having from 2 to 5 carbon atoms, or an alkenyloxycarbonyl group having from 3 to 5 carbon atoms.

As specific examples of the above-mentioned $R^3$, preferably mentioned are a formyl group; an alkylcarbonyl group, such as an acetyl group, a propionyl group, a butyryl group, an isobutyryl group, a pivaloyl group, a trifluoroacetyl group, etc.; an alkenylcarbonyl group, such as an acryloyl group, a methacryloyl group, a crotonoyl group, etc.; an alkynylcarbonyl group, such as a propioloyl group, etc.; an arylcarbonyl group, such as a benzoyl group, a 2-methylbenzoyl group, a 3-methylbenzoyl group, a 4-methylbenzoyl group, a 2,4-dimethylbenzoyl group, a 2,6-dimethylbenzoyl group, a 3,4-dimethylbenzoyl group, a 2,4,6-trimethylbenzoyl group, a 2-fluorobenzoyl group, a 3-fluorobenzoyl group, a 4-fluorobenzoyl group, a 2,4-difluorobenzoyl group, a 2,6-difluorobenzoyl group, a 3,4-difluorobenzoyl group, a 2,4,6-trifluorobenzoyl group, etc.; an alkoxycarbonyl group, such as a methoxycarbonyl group, an ethoxycarbonyl group, an n-propoxycarbonyl group, an n-butoxycarbonyl group, an isopropoxycarbonyl group, a tert-butoxycarbonyl group, a 3,3,3-trifluoroethoxycarbonyl group, etc.; an alkenyloxycarbonyl group, such as a vinyloxycarbonyl group, a 2-propenyloxycarbonyl group, a 2-butenyloxycarbonyl group, a 2-methyl-2-propenyloxycarbonyl group, a 3-methyl-2-butenyloxycarbonyl group, etc.; an alkynyloxycarbonyl group, such as a 2-propynyloxycarbonyl group, a 2-butynyloxycarbonyl group, a 3-butynyloxycarbonyl group, a 1-methyl-2-propynyloxycarbonyl group, a 1,1-dimethyl-2-propynyloxycarbonyl group, etc.; an aryloxycarbonyl group, such as a phenoxycarbonyl group, a 2-methylphenoxycarbonyl group, a 3-methylphenoxycarbonyl group, a 4-methylphenoxycarbonyl group, a 2,4-dimethylphenoxycarbonyl group, a 2,6-dimethylphenoxycarbonyl group, a 3,4-dimethylphenoxycarbonyl group, a 2,4,6-trimethylphenoxycarbonyl group, a 2-fluorophenoxycarbonyl group, a 3-fluorophenoxycarbonyl group, a 4-fluorophenoxycarbonyl group, a 2,4-difluorophenoxycarbonyl group, a 2,6-difluorophenoxycarbonyl group, a 3,4-difluorophenoxycarbonyl group, a 2,4,6-trifluorophenoxycarbonyl group, etc.; a 2,2-dioxide-1,2-oxathiolan-4-yloxycarbonyl group, a 2,2-dioxide-1,2-oxathian-4-yloxycarbonyl group; an alkylsulfonyl group, such as a methanesulfonyl group, an ethanesulfonyl group, a propane-1-sulfonyl group, a butane-1-sulfonyl group, a propane-2-sulfonyl group, a trifluoromethanesulfonyl group, a 2,2,2-trifluoroethanesulfonyl group, etc.; an arylsulfonyl group, such as a benzenesulfonyl group, a 4-methylbenzenesulfonyl group, a 4-chlorobenzenesulfonyl group, etc.; a dialkylphosphoryl group, such as a dimethylphosphoryl group, a diethylphosphoryl group, a dipropylphosphoryl group, etc.; analkoxy(alkyl)phosphoryl group, such as a methoxy(methyl)phosphoryl group, an ethoxy(ethyl)phosphoryl group, a propoxy(propyl)phosphoryl group, etc.; a dialkoxyphosphoryl group, such as a dimethoxyphosphoryl group, a diethoxyphosphoryl group, a dipropoxyphosphoryl group, etc.; an alkoxysulfinyl group, such as a group —S(O)—$OCH_3$, a group —S(O)—$OC_2H_5$, a 2,2-dioxide-1,2-oxathiolan-4-yloxysulfinyl group, a 2,2-dioxide-1,2-oxathian-4-yloxysulfinyl group, etc.; a 2-(dialkoxyphosphoryl)acetyl group, such as a group —C(O)$CH_2$P(O)($OCH_3$)$_2$, a group —C(O)$CH_2$P(O)($OC_2H_5$)$_2$, etc. Of those, more preferred are a formyl group, an acetyl group, a propionyl group, a pivaloyl group, an acryloyl group, a methacryloyl group, a crotonoyl group, a methoxycarbonyl group, an ethoxycarbonyl group, an n-propoxycarbonyl group, an isopropoxycarbonyl group, a tert-butoxycarbonyl group, a vinyloxycarbonyl group, a 2-propenyloxycarbonyl group, and a 2-propynyloxy group; and even more preferred are an acetyl group, a propionyl group, an isobutyryl group, a pivaloyl group, an acryloyl group, a methacryloyl group, a methoxycarbonyl group, an ethoxycarbonyl group, an isopropoxycarbonyl group, a tert-butoxycarbonyl group, a vinyloxycarbonyl group, and a 2-propenyloxycarbonyl group.

In the general formula (I), when the group —OS(=O)$_2$— is substituted with $OR^3$ at the β-position thereof, then the hydrolyzability of the compound is greatly lowered as compared with that of conventional cyclic sulfonic acid esters, and the case is especially preferred since the handleability of the compound is easy in air.

$R^4$ in the above-mentioned general formula (I) represents an alkyl group having from 1 to 6 carbon atoms, a 2,2-dioxide-1,2-oxathiolan-4-yl group, or a 2,2-dioxide-1,2-oxathian-4-yl group, and is preferably an alkyl group having 1 or 2 carbon atoms, or a 2,2-dioxide-1,2-oxathiolan-4-yl group.

As specific examples of the above-mentioned $R^4$, preferably mentioned are a methyl group, an ethyl group, an n-propyl group, an n-butyl group, an n-pentyl group, an n-hexyl group, an isopropyl group, a sec-butyl group, a tert-butyl group, a 2,2-dioxide-1,2-oxathiolan-4-yl group, and a 2,2-dioxide-1,2-oxathian-4-yl group. Above all, more preferred are a methyl group, an ethyl group, and a 2,2-dioxide-1,2-oxathiolan-4-yl group.

In the above-mentioned general formula (I), $R^5$ represents an alkyl group having from 1 to 6 carbon atoms, and is preferably an alkyl group having 1 or 2 carbon atoms.

As specific examples of the above-mentioned $R^5$, preferably mentioned are a methyl group, an ethyl group, an n-propyl group, an n-butyl group, an n-pentyl group, an n-hexyl group, an isopropyl group, a sec-butyl group, and a tert-butyl group. Above all, more preferred are a methyl group, and an ethyl group.

The compounds where the substituents fall within the above-mentioned ranges are preferred as capable of noticeably improving the electrochemical characteristics of batteries in a broad temperature range.

Concretely, the following compounds are mentioned as the cyclic sulfonic acid ester compound represented by the above-mentioned general formula (I).

(i) As the case where L is a divalent hydrocarbon group of an alkylene group having 2 or 3 carbon atoms in which at least one hydrogen atom is substituted with $OR^3$ and $R^3$ is a formyl group, an alkylcarbonyl group, an alkenylcarbonyl group, an alkynylcarbonyl group or an arylcarbonyl group:

Preferred are one or more selected from 2,2-dioxide-1,2-oxathiolan-3-yl formate, 2,2-dioxide-1,2-oxathiolan-4-yl formate, 2,2-dioxide-3-methyl-1,2-oxathiolan-4-yl formate, 2,2-dioxide-4-methyl-1,2-oxathiolan-4-yl formate, 2,2-dioxide-5-methyl-1,2-oxathiolan-4-yl formate, 2,2-dioxide-5-fluoro-1,2-oxathiolan-4-yl formate, 2,2-dioxide-1,2-oxathiolan-3-yl acetate, 2,2-dioxide-4-methyl-1,2-oxathiolan-3-yl acetate, 2,2-dioxide-5-methyl-1,2-oxathiolan-3-yl acetate, 2,2-dioxide-1,2-oxathiolan-4-yl acetate, 2,2-dioxide-3-methyl-1,2-oxathiolan-4-yl acetate, 2,2-dioxide-4-methyl-1,2-oxathiolan-4-yl acetate, 2,2-dioxide-5-methyl-1,2-oxathiolan-4-yl acetate, 2,2-dioxide-3-trifluoromethyl-1,2-oxathiolan-4-yl acetate, 2,2-dioxide-5-trifluoromethyl-1,2-oxathiolan-4-yl acetate, 2,2-dioxide-5-fluoro-1,2-oxathiolan-4-yl acetate, 2,2-dioxide-1,2-oxathiolan-3-yl propionate, 2,2-dioxide-1,2-oxathiolan-4-yl propionate, 2,2-dioxide-3-methyl-1,2-oxathiolan-4-yl propionate, 2,2-dioxide-4-methyl-1,2-oxathiolan-4-yl propionate, 2,2-dioxide-5-methyl-1,2-oxathiolan-4-yl propionate, 2,2-dioxide-5-fluoro-1,2-oxathiolan-4-yl propionate, 2,2-dioxide-1,2-oxathiolan-3-yl butyrate, 2,2-dioxide-1,2-oxathiolan-4-yl butyrate, 2,2-dioxide-3-methyl-1,2-oxathiolan-4-yl butyrate, 2,2-dioxide-4-methyl-1,2-oxathiolan-4-yl butyrate, 2,2-dioxide-5-methyl-1,2-oxathiolan-4-yl butyrate, 2,2-dioxide-5-fluoro-1,2-oxathiolan-4-yl butyrate, 2,2-dioxide-1,2-oxathiolan-4-yl isobutyrate, 2,2-dioxide-1,2-oxathiolan-3-yl isobutyrate, 2,2-dioxide-3-methyl-1,2-oxathiolan-4-yl isobutyrate, 2,2-dioxide-4-methyl-1,2-oxathiolan-4-yl isobutyrate, 2,2-dioxide-5-methyl-1,2-oxathiolan-4-yl isobutyrate, 2,2-dioxide-5-fluoro-1,2-oxathiolan-4-yl isobutyrate, 2,2-dioxide-1,2-oxathiolan-3-yl pivalate, 2,2-dioxide-1,2-oxathiolan-4-yl pivalate, 2,2-dioxide-3-methyl-1,2-oxathiolan-4-yl pivalate, 2,2-dioxide-4-methyl-1,2-oxathiolan-4-yl pivalate, 2,2-dioxide-5-methyl-1,2-oxathiolan-4-yl pivalate, 2,2-dioxide-5-fluoro-1,2-oxathiolan-4-yl pivalate, 2,2-dioxide-1,2-oxathiolan-3-yl trifluoroacetate, 2,2-dioxide-1,2-oxathiolan-4-yl trifluoroacetate, 2,2-dioxide-3-methyl-1,2-oxathiolan-4-yl trifluoroacetate, 2,2-dioxide-4-methyl-1,2-oxathiolan-4-yl trifluoroacetate, 2,2-dioxide-5-methyl-1,2-oxathiolan-4-yl trifluoroacetate, 2,2-dioxide-5-fluoro-1,2-oxathiolan-4-yl trifluoroacetate, 2,2-dioxide-1,2-oxathiolan-4-yl acrylate, 2,2-dioxide-1,2-oxathiolan-4-yl methacrylate, 2,2-dioxide-1,2-oxathiolan-4-yl crotonate, 2,2-dioxide-1,2-oxathiolan-4-yl propiolate, 2,2-dioxide-1,2-oxathiolan-4-yl benzoate, 2,2-dioxide-1,2-oxathiolan-4-yl 2-methylbenzoate, 2,2-dioxide-1,2-oxathiolan-4-yl 3-methylbenzoate, 2,2-dioxide-1,2-oxathiolan-4-yl 4-methylbenzoate, 2,2-dioxide-1,2-oxathiolan-4-yl 2,4-dimethylbenzoate, 2,2-dioxide-1,2-oxathiolan-4-yl 2,6-dimethylbenzoate, 2,2-dioxide-1,2-oxathiolan-4-yl 3,4-dimethylbenzoate, 2,2-dioxide-1,2-oxathiolan-4-yl 2,4,6-trimethylbenzoate, 2,2-dioxide-1,2-oxathiolan-4-yl 2-fluorobenzoate, 2,2-dioxide-1,2-oxathiolan-4-yl 3-fluorobenzoate, 2,2-dioxide-1,2-oxathiolan-4-yl 4-fluorobenzoate, 2,2-dioxide-1,2-oxathiolan-4-yl 2,4-difluorobenzoate, 2,2-dioxide-1,2-oxathiolan-4-yl 2,6-difluorobenzoate, 2,2-dioxide-1,2-oxathiolan-4-yl 3,4-difluorobenzoate, 2,2-dioxide-1,2-oxathiolan-4-yl 2,4,6-trifluorobenzoate, 2,2-dioxide-1,2-oxathian-3-yl formate, 2,2-dioxide-1,2-oxathian-4-yl formate, 2,2-dioxide-1,2-oxathian-3-yl acetate, 2,2-dioxide-1,2-oxathian-4-yl acetate, 2,2-dioxide-3-methyl-1,2-oxathian-4-yl acetate, 2,2-dioxide-6-methyl-1,2-oxathian-4-yl acetate, 2,2-dioxide-1,2-oxathian-3-yl propionate, 2,2-dioxide-1,2-oxathian-4-yl propionate, 2,2-dioxide-1,2-oxathian-3-yl butyrate, 2,2-dioxide-1,2-oxathian-4-yl butyrate, 2,2-dioxide-1,2-dioxathian-3-yl isobutyrate, 2,2-dioxide-1,2-oxathian-4-yl isobutyrate, 2,2-dioxide-1,2-oxathian-3-yl pivalate, 2,2-dioxide-1,2-oxathian-4-yl pivalate, 2,2-dioxide-1,2-oxathian-3-yl trifluoroacetate, 2,2-dioxide-1,2-oxathian-4-yl trifluoroacetate, 2,2-dioxide-1,2-oxathian-4-yl acrylate, 2,2-dioxide-1,2-oxathian-4-yl methacrylate, 2,2-dioxide-1,2-oxathian-4-yl crotonate, 2,2-dioxide-1,2-oxathian-4-yl propionate, 2,2-dioxide-1,2-oxathian-4-yl benzoate, 2,2-dioxide-1,2-oxathian-4-yl 4-methylbenzoate, 2,2-dioxide-1,2-oxathian-4-yl 2,4-dimethylbenzoate, 2,2-dioxide-1,2-oxathian-4-yl 2,4,6-trimethylbenzoate, 2,2-dioxide-1,2-oxathian-4-yl 4-fluorobenzoate, 2,2-dioxide-1,2-oxathian-4-yl 2,4-difluorobenzoate, and 2,2-dioxide-1,2-oxathian-4-yl 2,4,6-trifluorobenzoate.

(ii) As the case where L is a divalent hydrocarbon group of an alkylene group having 2 or 3 carbon atoms in which at least one hydrogen atom is substituted with $OR^3$ and $R^3$ is an alkoxycarbonyl group, an alkenyloxycarbonyl group, an alkynyloxycarbonyl group, an aryloxycarbonyl group, a 2,2-dioxide-1,2-oxathiolan-4-yloxycarbonyl group or a 2,2-dioxide-1,2-oxathian-4-yloxycarbonyl group:

Preferred are one or more selected from 2,2-dioxide-1,2-oxathiolan-3-yl methyl carbonate, 2,2-dioxide-4-methyl-1,2-oxathiolan-3-yl methyl carbonate, 2,2-dioxide-5-methyl-1,2-oxathiolan-3-yl methyl carbonate, 2,2-dioxide-1,2-oxathiolan-4-yl methyl carbonate, 2,2-dioxide-3-methyl-1,2-oxathiolan-4-yl methyl carbonate, 2,2-dioxide-4-methyl-1,2-oxathiolan-4-yl methyl carbonate, 2,2-dioxide-5-methyl-1,2-oxathiolan-4-yl methyl carbonate, 2,2-dioxide-3-trifluoromethyl-1,2-oxathiolan-4-yl methyl carbonate, 2,2-dioxide-5-trifluoromethyl-1,2-oxathiolan-4-yl methyl carbonate, 2,2-dioxide-5-fluoro-1,2-oxathiolan-4-yl methyl carbonate, 2,2-dioxide-1,2-oxathiolan-3-yl ethyl carbonate, 2,2-dioxide-1,2-oxathiolan-4-yl ethyl carbonate, 2,2-dioxide-3-methyl-1,2-oxathiolan-4-yl ethyl carbonate, 2,2-dioxide-4-methyl-1,2-oxathiolan-4-yl ethyl carbonate, 2,2-dioxide-5-methyl-1,2-oxathiolan-4-yl ethyl carbonate, 2,2-dioxide-5-fluoro-1,2-oxathiolan-4-yl ethyl carbonate, 2,2-dioxide-1,2-oxathiolan-3-yl propyl carbonate, 2,2-dioxide-1,2-oxathiolan-4-yl propyl carbonate, 2,2-dioxide-3-methyl-1,2-oxathiolan-4-yl propyl carbonate, 2,2-dioxide-4-methyl-1,2-oxathiolan-4-yl propyl carbonate, 2,2-dioxide-5-methyl-1,2-oxathiolan-4-yl propyl carbonate, 2,2-dioxide-5-fluoro-1,2-oxathiolan-4-yl propyl carbonate, butyl 2,2-dioxide-1,2-oxathiolan-3-yl carbonate, butyl 2,2-dioxide-1,2-oxathiolan-4-yl carbonate, butyl 2,2-dioxide-3-methyl-1,2-oxathiolan-4-yl carbonate, butyl 2,2-dioxide-5-methyl-1,2-oxathiolan-4-yl carbonate, 2,2-dioxide-1,2-oxathiolan-3-yl isopropyl carbonate, 2,2-dioxide-1,2-oxathiolan-4-yl isopropyl carbonate, 2,2-dioxide-3-methyl-1,2-oxathiolan-4-yl isopropyl carbonate, 2,2-dioxide-5-methyl-1,2-oxathiolan-4-yl isopropyl carbonate, tert-butyl 2,2-dioxide-1,2-oxathiolan-3-yl carbonate, tert-butyl 2,2-dioxide-1,2-oxathiolan-4-yl carbonate, tert-butyl 2,2-dioxide-3-methyl-1,2-oxathiolan-4-yl carbonate, tert-butyl 2,2-dioxide-5-methyl-1,2-oxathiolan-4-yl carbonate, 2,2-dioxide-1,2-oxathiolan-3-yl 2,2,2-trifluoroethyl carbonate, 2,2-dioxide-1,2-oxathiolan-4-yl 2,2,2-trifluoroethyl carbonate, 2,2-dioxide-3-methyl-1,2-oxathiolan-4-yl 2,2,2-trifluoroethyl carbonate, 2,2-dioxide-5-methyl-1,2-oxathiolan-4-yl 2,2,2-trifluoroethyl carbonate, 2,2-dioxide-1,2-oxathiolan-4-yl vinyl carbonate, 2,2-dioxide-1,2-oxathiolan-3-yl 2-propenyl carbonate, 2,2-dioxide-1,2-oxathiolan-4-yl 2-propenyl carbonate, 2-butenyl 2,2-dioxide-1,2-oxathiolan-4-yl carbonate, 2,2-dioxide-1,2-oxathiolan-4-yl 2-methyl-2-propenyl carbonate, 2,2-dioxide-1,2-oxathiolan-3-yl 2-propynyl carbonate, 2,2-dioxide-1,2-oxathiolan-4-yl 2-propynyl carbonate, 2-butynyl 2,2-dioxide-1,2-oxathiolan-4-yl carbonate, 3-butynyl 2,2-dioxide-1,2-oxathiolan-4-yl carbonate, 2,2-dioxide-1,2-oxathiolan-4-yl 1-methyl-2-propynyl carbonate, 2,2-dioxide-1,2-oxathiolan-4-yl 1,1-dimethyl-2-propynyl carbonate, 2,2-dioxide-1,2-oxathiolan-3-yl phenyl carbonate, 2,2-dioxide-1,2-oxathiolan-4-yl phenyl carbonate, 2,2-dioxide-1,2-oxathiolan-4-yl 2-methylphenyl carbonate, 2,2-dioxide-1,2-oxathiolan-4-yl 3-methylphenyl carbonate, 2,2-dioxide-1,2-oxathiolan-4-yl 4-methylphenyl carbonate, 2,4-dimethylphenyl 2,2-dioxide-1,2-oxathiolan-4-yl carbonate, 2,6-dimethylphenyl 2,2-dioxide-1,2-oxathiolan-4-yl carbonate, 3,4-dimethylphenyl 2,2-dioxide-1,2-oxathiolan-4-yl carbonate, 2,2-dioxide-1,2-oxathiolan-4-yl-2,4,6-trimethylphenylcarbonate, 2,2-dioxide-1,2-oxathiolan-4-yl 2-fluorophenyl carbonate, 2,2-dioxide-1,2-oxathiolan-4-yl 3-fluorophenyl carbonate, 2,2-dioxide-1,2-oxathiolan-4-yl 4-fluorophenyl carbonate, 2,4-difluorophenyl 2,2-dioxide-1,2-oxathiolan-4-yl carbonate, 2,6-difluorophenyl 2,2-dioxide-1,2-oxathiolan-4-yl carbonate, 3,4-difluorophenyl 2,2-dioxide-1,2-oxathiolan-4-yl carbonate, 2,2-dioxide-1,2-oxathiolan-4-yl-2,4,6-trifluorophenyl carbonate, bis(2,2-dioxide-1,2-oxathiolan-4-yl) carbonate, 2,2-dioxide-1,2-oxathian-3-yl methyl carbonate, 2,2-dioxide-4-methyl-1,2-oxathian-3-yl methyl carbonate, 2,2-dioxide-6-methyl-1,2-oxathian-3-yl methyl carbonate, 2,2-dioxide-1,2-oxathian-4-yl methyl carbonate, 2,2-dioxide-3-methyl-1,2-oxathian-4-yl methyl carbonate, 2,2-dioxide-6-methyl-1,2-oxathian-4-yl methyl carbonate, 2,2-dioxide-1,2-oxathian-3-yl ethyl carbonate, 2,2-dioxide-1,2-oxathian-4-yl ethyl carbonate, 2,2-dioxide-1,2-oxathian-3-yl propyl carbonate, 2,2-dioxide-1,2-oxathian-4-yl propyl carbonate, butyl 2,2-dioxide-1,2-oxathian-3-yl carbonate, butyl 2,2-dioxide-1,2-oxathian-4-yl carbonate, 2,2-dioxide-1,2-oxathian-3-yl isopropyl carbonate, 2,2-dioxide-1,2-oxathian-4-yl isopropyl carbonate, tert-butyl 2,2-dioxide-1,2-oxathian-3-yl carbonate, tert-butyl 2,2-dioxide-1,2-oxathian-4-yl carbonate, 2,2-dioxide-1,2-oxathian-3-yl 2,2,2-trifluoroethyl carbonate, 2,2-dioxide-1,2-oxathian-4-yl 2,2,2-trifluoroethyl carbonate, 2,2-dioxide-1,2-oxathian-4-yl vinyl carbonate, 2,2-dioxide-1,2-oxathian-4-yl 2-propenyl carbonate, 2-butenyl 2,2-dioxide-1,2-oxathian-4-yl carbonate, 2,2-dioxide-1,2-oxathian-4-yl 2-methyl-2-propenyl carbonate, 2,2-dioxide-1,2-oxathian-4-yl 2-propynyl carbonate, 2-butynyl 2,2-dioxide-1,2-oxathian-4-yl carbonate, 3-butynyl 2,2-dioxide-1,2-oxathian-4-yl carbonate, 2,2-dioxide-1,2-oxathian-4-yl 1-methyl-2-propynyl carbonate, 2,2-dioxide-1,2-oxathian-4-yl-1,1-dimethyl-2-propynylcarbonate, 2,2-dioxide-1,2-oxathian-4-yl phenyl carbonate, 2,2-dioxide-1,2-oxathian-4-yl 4-methylphenyl carbonate, 2,4-dimethylphenyl 2,2-dioxide-1,2-oxathian-4-yl carbonate, 2,2-dioxide-1,2-oxathian-4-yl 2,4,6-trimethylphenyl carbonate, 2,2-dioxide-1,2-oxathian-4-yl 4-fluorophenyl carbonate, 2,4-difluorophenyl 2,2-dioxide-1,2-oxathian-4-yl carbonate, 2,2-dioxide-1,2-oxathian-4-yl 2,4,6-trifluorophenyl carbonate, and bis(2,2-dioxide-1,2-oxathian-4-yl) carbonate.

(iii) As the case where L is a divalent hydrocarbon group of an alkylene group having 2 or 3 carbon atoms in which at least one hydrogen atom is substituted with $OR^3$ and $R^3$ is an alkanesulfonyl group or an arylsulfonyl group:

Preferred are one or more selected from 2,2-dioxide-1,2-oxathiolan-3-yl methanesulfonate, 2,2-dioxide-1,2-oxathiolan-4-yl methanesulfonate, 2,2-dioxide-1,2-oxathiolan-4-yl ethanesulfonate, 2,2-dioxide-1,2-oxathiolan-4-yl propane-1-sulfonate, 2,2-dioxide-1,2-oxathiolan-4-yl butane-1-sulfonate, 2,2-dioxide-1,2-oxathiolan-4-yl propane-2-sulfonate, 2,2-dioxide-1,2-oxathiolan-4-yl trifluoromethanesulfonate, 2,2-dioxide-1,2-oxathiolan-4-yl 2,2,2-trifluoroethanesulfonate, 2,2-dioxide-1,2-oxathiolan-3-yl benzenesulfonate, 2,2-dioxide-1,2-oxathiolan-4-yl benzenesulfonate, 2,2-dioxide-1,2-oxathiolan-3-yl 4-methylbenzenesulfonate, 2,2-dioxide-1,2-oxathiolan-4-yl 4-methylbenzenesulfonate, 2,2-dioxide-1,2-oxathiolan-4-yl 4-chlorobenzenesulfonate, 2,2-dioxide-1,2-oxathian-4-yl methanesulfonate, 2,2-dioxide-1,2-oxathian-4-yl ethanesulfonate, 2,2-dioxide-1,2-oxathian-4-yl propane-1-sulfonate, 2,2-dioxide-1,2-oxathian-4-yl butane-1-sulfonate, 2,2-dioxide-1,2-oxathian-4-yl propane-2-sulfonate, 2,2-dioxide-1,2-oxathian-4-yl trifluoromethanesulfonate, 2,2-dioxide-1,2-oxathian-4-yl 2,2,2-trifluoroethanesulfonate, 2,2-dioxide-1,2-oxathian-4-yl benzenesulfonate, 2,2-dioxide-1,2-oxathian-4-yl 4-methylbenzenesulfonate, and 2,2-dioxide-1,2-oxathian-4-yl 4-chlorobenzenesulfonate.

(iv) As the case where L is a divalent hydrocarbon group of an alkylene group having 2 or 3 carbon atoms in which at least one hydrogen atom is substituted with $OR^3$ and $R^3$ is a dialkylphosphoryl group, an alkoxy(alkyl)phosphoryl group or a dialkoxyphosphoryl group:

Preferred are one or more selected from 2,2-dioxide-1,2-oxathiolan-3-yl dimethylphosphinate, 2,2-dioxide-1,2-oxathiolan-4-yl dimethylphosphinate, 2,2-dioxide-1,2-oxathiolan-4-yl diethylphosphinate, 2,2-dioxide-1,2-oxathiolan-4-yl dipropylphosphinate, 2,2-dioxide-1,2-oxathiolan-3-yl methyl methylphosphonate, 2,2-dioxide-1,2-oxathiolan-4-yl methyl methylphosphonate, 2,2-dioxide-1,2-oxathiolan-4-yl ethyl ethylphosphonate, 2,2-dioxide-1,2-oxathiolan-4-yl propyl propylphosphonate, 2,2-dioxide-1,2-oxathiolan-4-yl dimethylphosphate, 2,2-dioxide-1,2-oxathiolan-3-yl diethylphosphate, 2,2-dioxide-1,2-oxathiolan-4-yl diethylphosphate, 2,2-dioxide-1,2-oxathiolan-4-yl dipropylphosphate, 2,2-dioxide-1,2-oxathian-4-yl dimethylphosphinate, 2,2-dioxide-1,2-oxathian-4-yl diethylphosphinate, 2,2-dioxide-1,2-oxathian-4-yl dipropylphosphinate, 2,2-dioxide-1,2-oxathian-4-yl methyl methylphosphonate, 2,2-dioxide-1,2-oxathian-4-yl ethyl ethylphosphonate, 2,2-dioxide-1,2-oxathian-4-yl propyl propylphosphonate, 2,2-dioxide-1,2-oxathian-4-yl dimethylphosphate, 2,2-dioxide-1,2-oxathian-4-yl diethylphosphate, and 2,2-dioxide-1,2-oxathian-4-yl dipropylphosphate.

(v) As the case where L is a divalent hydrocarbon group of an alkylene group having 2 or 3 carbon atoms in which at least one hydrogen atom is substituted with $OR^3$ and $R^3$ is an alkoxysulfinyl group or a group —C(O)CH$_2$P(O)(OR$^5$)$_2$:

Preferred are one or more selected from 2,2-dioxide-1,2-oxathiolan-3-yl methyl sulfite, 2,2-dioxide-1,2-oxathiolan-4-yl methyl sulfite, 2,2-dioxide-1,2-oxathiolan-4-yl ethyl sulfite, 2,2-dioxide-1,2-oxathiolan-4-yl propyl sulfite, bis(2,2-dioxide-1,2-oxathiolan-4-yl) sulfite, 2,2-dioxide-1,2-oxathiolan-4-yl 2-(dimethoxyphosphoryl)acetate, 2,2-dioxide-1,2-oxathiolan-3-yl 2-(diethoxyphosphoryl)acetate, 2,2-dioxide-1,2-oxathiolan-4-yl 2-(diethoxyphosphoryl)acetate, 2,2-dioxide-1,2-oxathian-4-yl methyl sulfite, 2,2-dioxide-1,2-oxathian-4-yl ethyl sulfite, 2,2-dioxide-1,2-oxathian-4-yl propyl sulfite, bis(2,2-dioxide-1,2-oxathian-4-yl) sulfite, 2,2-dioxide-1,2-oxathian-4-yl 2-(dimethoxyphosphoryl)acetate, and 2,2-dioxide-1,2-oxathian-4-yl 2-(diethoxyphosphoryl)acetate.

(vi) As the case where L is a divalent hydrocarbon group of an alkylene group having 2 or 3 carbon atoms in which at least one methylene ($CH_2$) is substituted with C(=O):

Preferred are one or more selected from 1,2-oxathiolan-4-one 2,2-dioxide, 5-methyl-1,2-oxathiolan-4-one 2,2-dioxide, 3,5-dimethyl-1,2-oxathiolan-4-one 2,2-dioxide, 5,5-dimethyl-1,2-oxathiolan-4-one 2,2-dioxide, 3,5,5-trimethyl-1,2-oxathiolan-4-one 2,2-dioxide, 3,3,5,5-tetramethyl-1,2-oxathiolan-4-one 2,2-dioxide, 5-methyl-3-tri fluoromethyl-1,2-oxathiolan-4-one 2,2-dioxide, 5,5-dimethyl-3-trifluoromethyl-1,2-oxathiolan-4-one 2,2-dioxide, 5-ethyl-1,2-oxathiolan-4-one 2,2-dioxide, 5,5-diethyl-1,2-oxathiolan-4-one-2,2-dioxide, 1,2-oxathian-4-one 2,2-dioxide, 6-methyl-1,2-oxathian-4-one 2,2-dioxide, 3,6-dimethyl-1,2-oxathian-4-one 2,2-dioxide, 6,6-dimethyl-1,2-oxathian-4-one 2,2-dioxide, and 6,6-dimethyl-3-trifluoromethyl-1,2-oxathian-4-one 2,2-dioxide.

Of the cyclic sulfonic ester compounds of the above-mentioned (i) to (vi), preferred are one or more selected from 2,2-dioxide-1,2-oxathiolan-4-yl formate, 2,2-dioxide-3-methyl-1,2-oxathiolan-4-yl formate, 2,2-dioxide-5-methyl-1,2-oxathiolan-4-yl formate, 2,2-dioxide-1,2-oxathiolan-4-yl acetate, 2,2-dioxide-3-methyl-1,2-oxathiolan-4-yl acetate, 2,2-dioxide-5-methyl-1,2-oxathiolan-4-yl acetate, 2,2-dioxide-1,2-oxathiolan-4-yl propionate, 2,2-dioxide-3-methyl-1,2-oxathiolan-4-yl propionate, 2,2-dioxide-5-methyl-1,2-oxathiolan-4-yl propionate, 2,2-dioxide-1,2-oxathiolan-4-yl butyrate, 2,2-dioxide-3-methyl-1,2-oxathiolan-4-yl butyrate, 2,2-dioxide-5-methyl-1,2-oxathiolan-4-yl butyrate, 2,2-dioxide-1,2-oxathiolan-4-yl isobutyrate, 2,2-dioxide-3-methyl-1,2-oxathiolan-4-yl isobutyrate, 2,2-dioxide-5-methyl-1,2-oxathiolan-4-yl isobutyrate, 2,2-dioxide-1,2-oxathiolan-4-yl pivalate, 2,2-dioxide-3-methyl-1,2-oxathiolan-4-yl pivalate, 2,2-dioxide-5-methyl-1,2-oxathiolan-4-yl pivalate, 2,2-dioxide-1,2-oxathiolan-4-yl acrylate, 2,2-dioxide-1,2-oxathiolan-4-yl methacrylate, 2,2-dioxide-1,2-oxathiolan-4-yl crotonate, 2,2-dioxide-1,2-oxathian-4-yl formate, 2,2-dioxide-1,2-oxathian-4-yl acetate, 2,2-dioxide-1,2-oxathian-4-yl propionate, 2,2-dioxide-1,2-oxathian-4-yl butyrate, 2,2-dioxide-1,2-oxathian-4-yl isobutyrate, 2,2-dioxide-1,2-oxathian-4-yl pivalate, 2,2-dioxide-1,2-oxathiolan-4-yl methyl carbonate, 2,2-dioxide-3-methyl-1,2-oxathiolan-4-yl methyl carbonate, 2,2-dioxide-5-methyl-1,2-oxathiolan-4-yl methyl carbonate, 2,2-dioxide-1,2-oxathiolan-4-yl ethyl carbonate, 2,2-dioxide-3-methyl-1,2-oxathiolan-4-yl ethyl carbonate, 2,2-dioxide-5-methyl-1,2-oxathiolan-4-yl ethyl carbonate, 2,2-dioxide-1,2-oxathiolan-4-yl propyl carbonate, 2,2-dioxide-3-methyl-1,2-oxathiolan-4-yl propyl carbonate, 2,2-dioxide-5-methyl-1,2-oxathiolan-4-yl propyl carbonate, 2,2-dioxide-1,2-oxathiolan-4-yl isopropyl carbonate, 2,2-dioxide-3-methyl-1,2-oxathiolan-4-yl isopropyl carbonate, 2,2-dioxide-5-methyl-1,2-oxathiolan-4-yl isopropyl carbonate, tert-butyl 2,2-dioxide-1,2-oxathiolan-4-yl carbonate, tert-butyl 2,2-dioxide-3-methyl-1,2-oxathiolan-4-yl carbonate, tert-butyl 2,2-dioxide-5-methyl-1,2-oxathiolan-4-yl carbonate, 2,2-dioxide-1,2-oxathiolan-4-yl vinyl carbonate, 2,2-dioxide-1,2-oxathiolan-4-yl 2-propenyl carbonate, 2,2-dioxide-1,2-oxathiolan-4-yl dimethylphosphate, 2,2-dioxide-1,2-oxathiolan-4-yl diethylphosphate, bis(2,2-dioxide-1,2-oxathiolan-4-yl) sulfite, 2,2-dioxide-1,2-oxathiolan-4-yl 2-(dimethoxyphosphoryl)acetate, 2,2-dioxide-1,2-oxathiolan-4-yl 2-(diethoxyphosphoryl)acetate, 1,2-oxathiolan-4-one 2,2-dioxide, 5-methyl-1,2-oxathiolan-4-one 2,2-dioxide, 5,5-dimethyl-1,2-oxathiolan-4-one 2,2-dioxide, 5-methyl-1,2-oxathian-4-one 2,2-dioxide, and 6,6-dimethyl-1,2-oxathian-4-one 2,2-dioxide.

More preferred are one or more selected from 2,2-dioxide-1,2-oxathiolan-4-yl formate, 2,2-dioxide-1,2-oxathiolan-4-yl acetate, 2,2-dioxide-1,2-dioxathiolan-4-yl propionate, 2,2-dioxide-1,2-oxathiolan-4-yl isobutyrate, 2,2-dioxide-1,2-oxathiolan-4-yl pivalate, 2,2-dioxide-1,2-oxathiolan-4-yl acrylate, 2,2-dioxide-1,2-oxathiolan-4-yl methacrylate, 2,2-dioxide-1,2-oxathian-4-yl acetate, 2,2-dioxide-1,2-oxathiolan-4-yl methyl carbonate, 2,2-dioxide-1,2-oxathiolan-4-yl ethyl carbonate, 2,2-dioxide-1,2-oxathiolan-4-yl isopropyl carbonate, tert-butyl 2,2-dioxide-1,2-oxathiolan-4-yl carbonate, 2,2-dioxide-1,2-oxathiolan-4-yl vinyl carbonate, 2,2-dioxide-1,2-oxathiolan-4-yl diethylphosphate, bis(2,2-dioxide-1,2-oxathiolan-4-yl) sulfite, 2,2-dioxide-1,2-oxathiolan-4-yl 2-(diethoxyphosphoryl)acetate, 1,2-oxathiolan-4-one 2,2-dioxide, 5-methyl-1,2-oxathiolan-4-one 2,2-dioxide, 5,5-dimethyl-1,2-oxathiolan-4-one 2,2-dioxide, and 6,6-dimethyl-1,2-oxathian-4-one 2,2-dioxide.

In the nonaqueous electrolytic solution of the present invention, the content of the cyclic sulfonic acid ester compound represented by the above-mentioned general formula (I) is preferably from 0.001 to 10% by mass of the nonaqueous electrolytic solution. When the content is at most 10% by mass, then the risk of excessive formation of a surface film on the electrode to worsen the low-temperature load characteristics of batteries could be low; and when at least 0.001% by mass, then the surface film formation would be sufficient and the effect of improving high-temperature storage characteristics could be enhanced. The content is more preferably at least 0.05% by mass of the nonaqueous electrolytic solution, even more preferably at least 0.2% by mass, and its upper limit is preferably at most 8% by mass, more preferably at most 5% by mass, even more preferably at most 2% by mass.

In the nonaqueous electrolytic solution of the present invention, combining the cyclic sulfonic acid ester compound represented by the above-mentioned general formula (I) with the nonaqueous solvent, electrolyte salt and other additives to be mentioned below exhibits a specific effect of synergistically improving the electrochemical characteristics of batteries in a broad temperature range.

[Nonaqueous Solvent]

As the nonaqueous solvent for use in the nonaqueous electrolytic solution of the present invention, there may be mentioned one or more selected from cyclic carbonates, linear esters, lactones, ethers, and amides. Preferably, the solvent contains both a cyclic carbonate and a linear ester.

The term "linear ester" is used here as a concept including linear carbonates and linear carboxylates.

As the cyclic carbonates, there may be mentioned one or more selected from ethylene carbonate (EC), propylene carbonate (PC), 1,2-butylene carbonate, 2,3-butylene carbonate, 4-fluoro-1,3-dioxolan-2-one (FEC), trans or cis-4,5-difluoro-1,3-dioxolan-2-one (hereinafter the two are collectively called "DFEC"), vinylene carbonate (VC), and vinylethylene carbonate (VEC).

Of those, preferred is use of at least one cyclic carbonate having a carbon-carbon double bond or a fluorine atom, as markedly enhancing low-temperature load characteristics after high-temperature charging storage; and more preferred is use of both a cyclic carbonate having a carbon-carbon double bond and a cyclic carbonate having a fluorine atom. As the cyclic carbonate having a carbon-carbon double bond, more preferred are VC and VEC; and as the cyclic carbonate having a fluorine atom, more preferred are FEC and DFEC.

The content of the carbon-carbon double bond-containing cyclic carbonate is preferably at least 0.07% by volume relative to the total volume of the nonaqueous solvent, more preferably at least 0.2% by volume, even more preferably at least 0.7% by volume, and the upper limit thereof is preferably at most 7% by volume, more preferably at most 4% by volume, even more preferably at most 2.5% by volume. Falling within the range, the stability of the surface film during high-temperature storage can be markedly enhanced not detracting from the low-temperature Li ion permeability thereof.

The content of the fluorine atom-containing cyclic carbonate is preferably at least 0.07% by volume relative to the total volume of the nonaqueous solvent, more preferably at least 4% by volume, even more preferably at least 7% by volume, and the upper limit thereof is preferably at most 35% by volume, more preferably at most 25% by volume, even more preferably at most 15% by volume. Falling within the range, the stability of the surface film during high-temperature storage can be markedly enhanced not detracting from the low-temperature Li ion permeability thereof.

In case where the nonaqueous solvent contains both a carbon-carbon double bond-containing cyclic carbonate and a fluorine atom-containing cyclic carbonate, the content of the carbon-carbon double bond-containing cyclic carbonate relative to the content of the fluorine atom-containing cyclic carbonate is preferably at least 0.2% by volume, more preferably at least 3% by volume, even more preferably at least 7% by volume, and its upper limit is preferably at most 40% by volume, more preferably at most 30% by volume, even more preferably at most 15% by volume. Falling within the range, the stability of the surface film during high-temperature storage can be markedly enhanced not detracting from the low-temperature Li ion permeability thereof.

Preferably, the nonaqueous solvent contains ethylene carbonate and/or propylene carbonate, as the resistance of the surface film formed on electrodes can be reduced. Preferably, the content of ethylene carbonate and/or propylene carbonate is at least 3% by volume relative to the total volume of the nonaqueous solvent, more preferably at least 5% by volume, even more preferably at least 7% by volume, and its upper limit is preferably at most 45% by volume, more preferably at most 35% by volume, even more preferably at most 25% by volume.

One kind of those solvents may be used, but using two or more different kinds thereof as combined is preferred as further enhancing the electrochemical characteristics in a broad temperature range. Even more preferably, three or more different kinds are combined. Preferred combinations of the cyclic carbonates include EC and PC; EC and VC; PC and VC; VC and FEC; EC and FEC; PC and FEC; FEC and DFEC; EC and DFEC; PC and DFEC; VC and DFEC; VEC and DFEC; EC and PC and VC; EC and PC and FEC; EC and VC and FEC; EC and VC and VEC; PC and VC and FEC; EC and VC and DFEC; PC and VC and DFEC; EC and PC and VC and FEC; EC and PC and VC and DFEC; etc. Of those combinations, more preferred combinations are EC and VC; EC and FEC; PC and FEC; EC and PC and VC; EC and PC and FEC; EC and VC and FEC; PC and VC and FEC; EC and PC and VC and FEC; etc.

As the linear esters, preferably mentioned are one or more asymmetric linear carbonates selected from methyl ethyl carbonate (MEC), methyl propyl carbonate (MPC), methyl isopropyl carbonate (MIPC), methyl butyl carbonate, and ethyl propyl carbonate; one or more symmetric linear carbonates selected from dimethyl carbonate (DMC), diethyl carbonate (DEC), dipropyl carbonate, dibutyl carbonate; and one or more linear carboxylates selected from pivalates, such as methyl pivalate, ethyl pivalate, propyl pivalate, etc., and methyl propionate, ethyl propionate, methyl acetate and ethyl acetate.

Of the above-mentioned linear esters, preferred are methyl group-having linear esters selected from dimethyl carbonate, methyl ethyl carbonate, methyl propyl carbonate, methyl isopropyl carbonate, methyl butyl carbonate, methyl propionate, methyl acetate and ethyl acetate; and more preferred are methyl group-having linear carbonates.

Preferably, two or more different types of linear carbonates are used here. More preferably, a combination of a symmetric linear carbonate and an asymmetric linear carbonate is used; and even more preferably, the content of the symmetric linear carbonate is larger than that of the asymmetric linear carbonate.

Not specifically defined, the content of the linear ester is preferably within a range of from 60 to 90% by volume relative to the total volume of the nonaqueous solvent. When the content is at least 60% by volume, then the risk of increasing the viscosity of the nonaqueous electrolytic solution may be low; and when at most 90% by volume, then the risk of lowering the electric conductivity of the nonaqueous electrolytic solution to worsen the electrochemical characteristics in a broad temperature range may be low. For these reasons, the above-mentioned range is preferred here.

The ratio by volume of the symmetric linear carbonate to the linear carbonate is preferably at least 51% by volume, more preferably at least 55% by volume, and its upper limit is preferably at most 95% by volume, more preferably at most 85% by volume. Especially preferably, the symmetric linear carbonate for use herein contains dimethyl carbonate. Also preferably, the asymmetric linear carbonate for use herein has a methyl group, and especially preferred is use of methyl ethyl carbonate here.

The above-mentioned embodiments are preferred as enhancing the electrochemical characteristics of batteries in a markedly broad temperature range.

The ratio of the cyclic carbonate to the linear ester, cyclic carbonate/linear ester (by volume) is preferably from 10/90 to 45/55, more preferably from 15/85 to 40/60, even more preferably from 20/80 to 35/65, from the viewpoint of enhancing the electrochemical characteristics in a broad temperature range.

As other nonaqueous solvents for use herein, preferably mentioned are one or more selected from cyclic ethers, such as tetrahydrofuran, 2-methyltetrahydrofuran, 1,3-dioxolane, 1,3-dioxane, 1,4-dioxane, etc.; linear ethers, such as 1,2-dimethoxyethane, 1,2-diethoxyethane, 1,2-dibutoxyethane, etc.; amides, such as dimethylformamide, etc.; sulfones, such as sulfolane, etc.; lactones, such as γ-butyrolactone, γ-valerolactone, α-angelicalactone, etc.

In general, the above-mentioned nonaqueous solvents are combined and used as a mixture thereof for attaining suitable physical properties. Preferred combinations include, for example, a combination of a cyclic carbonate and a linear carbonate, a combination of a cyclic carbonate and a linear carboxylate, a combination of a cyclic carbonate, a linear carbonate and a lactone, a combination of a cyclic carbonate, a linear carbonate and an ether, a combination of acyclic carbonate, a linear carbonate and a linear carboxylate, etc.

For enhancing the electrochemical characteristics in a markedly broad temperature range, preferably, some other additives are further added to the nonaqueous electrolytic solution.

As specific examples of the other additives, preferably mentioned are one or more phosphates selected from trimethyl phosphate, tributyl phosphate and trioctyl phosphate; one or more nitriles selected from acetonitrile, propionitrile, succinonitrile, glutaronitrile, adiponitrile, and pimelonitrile; one or more isocyanates selected from tetramethylene diisocyanate, hexamethylene diisocyanate, and octamethylene diisocyanate; one or more triple bond-containing compounds selected from 2-propynyl methyl carbonate, 2-propynyl acetate, 2-propynyl formate, 2-propynyl methacrylate, 2-propynyl methanesulfonate, di(2-propynyl) oxalate, di(2-propynyl) glutamate, 2-butyne-1,4-diyl dimethanesulfonate, 2-butyne-1,4-diyl diformate, and 2,4-hexadiyne-1,6-diyl dimethanesulfonate; one or more S=O bond-containing compounds selected from sultone compounds, such as 1,3-propanesultone, 1,3-butanesultone, 2,4-butanesultone, 1,4-butanesultone, etc., cyclic sulfite compounds, such as ethylene sulfite, hexahydrobenzo[1.3.2]dioxathiolane-2-oxide (also referred to as 1,2-cyclohexanediol cyclic sulfite), 5-vinyl-hexahydro-1,3,2-benzodioxathiol-2-oxide, etc., sulfonic acid ester compounds, such as butane-2,3-diyl dimethanesulfonate, butane-1,4-diyl dimethanesulfonate, methylenemethane disulfonate, etc., vinyl sulfone compounds, such as divinyl sulfone, 1,2-bis(vinylsulfonyl)ethane, bis(2-vinylsulfonylethyl)ether, etc.; as well as one or more selected from linear carboxylic acid anhydrides, such as acetic anhydride, propionic anhydride, etc., cyclic acid anhydrides, such as succinic anhydride, maleic anhydride, glutaric anhydride, itaconic anhydride, 3-sulfo-propionic anhydride, etc., cyclic phosphazene compounds, such as methoxypentafluorocyclotriphosphazene, ethoxypentafluorocyclotriphosphazene, phenoxypentafluorocyclotriphosphazene, ethoxyheptafluorocyclotetraphosphazene, etc., branched alkyl group-having aromatic compounds, such as cyclohexylbenzene, fluorocyclohexylbenzene compounds (including 1-fluoro-2-cyclohexylbenzene, 1-fluoro-3-cyclohexylbenzene, and 1-fluoro-4-cyclohexylbenzene), tert-butylbenzene, tert-amylbenzene, 1-fluoro-4-tert-butylbenzene, etc., and other aromatic compounds, such as biphenyl, terphenyls (o-, m-, and p-form), diphenyl ether, fluorobenzene, difluorobenzenes (o-, m-, and p-form), anisole, 2,4-difluoroanisole, partially hydrogenated terphenyls (including 1,2-dicyclohexylbenzene, 2-phenylbicyclohexyl, 1,2-diphenylcyclohexane, o-cyclohexylbiphenyl), etc.

Of the above, preferred are nitriles and/or aromatic compounds as enhancing the electrochemical characteristics in a markedly broad temperature range. Of the nitriles, more preferred are one or more selected from succinonitrile, glutaronitrile, adiponitrile and pimelonitrile. Of the aromatic compounds, preferred are one or more selected from biphenyl, cyclohexylbenzene, tert-butylbenzene and tert-amylbenzene. The content of the nitrile and/or the aromatic compound is preferably from 0.001 to 5% by mass in the nonaqueous electrolytic solution. Within the range, a sufficient film could be formed not growing excessively and the effect thereof for enhancing the electrochemical characteristics in a broad temperature range can be augmented. The content is more preferably at least 0.005% by mass, even more preferably at least 0.01% by mass, still more preferably at least 0.03% by mass in the nonaqueous electrolytic solution, and its upper limit is preferably at most 3% by mass, more preferably at most 1% by mass, even more preferably at most 0.4% by mass.

In addition, containing (A) a triple bond-containing compound and (B) a cyclic or linear S=O group-containing compound selected from sultones, cyclic sulfites, sulfonic acid esters and vinylsulfones is preferred as enhancing the electrochemical characteristics in a markedly broad temperature range.

As the triple bond-containing compound (A), preferred are one or more selected from 2-propynyl methyl carbonate, 2-propynyl methacrylate, 2-propynyl methanesulfonate, di(2-propynyl) oxalate and 2-butyne-1,4-diyl dimethanesulfonate; and more preferred are one or more selected from 2-propynyl methanesulfonate, di(2-propynyl) oxalate and 2-butyne-1,4-diyl dimethanesulfonate.

The content of the triple bond-containing compound is preferably from 0.001 to 5% by mass in the nonaqueous electrolytic solution. When the content is at least 0.001% by mass, surface film formation would be enough and the effect of enhancing high-temperature cycle characteristics could be augments. The content is more preferably at least 0.005% by mass, even more preferably at least 0.01% by mass, still more preferably at least 0.03% by mass in the nonaqueous electrolytic solution, and its upper limit is preferably at most 3% by mass, more preferably at most 1% by mass, even more preferably at most 0.7% by mass.

As the cyclic S=O group-containing compound (not including tripe bond compounds and the compounds defined by the general formula (I)), preferred are one or more selected from 1,3-propanesultone, 1,3-butanesultone, 1,4-butanesultone, 2,4-butanesultone, methylenemethane disulfonate, ethylene sulfite and 4-(methylsulfonylmethyl)-1,3,2-dioxathiolane-2-oxide; and more preferred are one or more selected from 1,3-propanesultone, 1,4-butanesultone and 2,4-butanesultone.

As the linear S=O group-containing compound, preferred are one or more selected from butane-2,3-diyl dimethanesulfonate, butane-1,4-diyl dimethanesulfonate, dimethyl methanedisulfonate, pentafluorophenyl methanesulfonate, divinyl sulfone, and bis(2-vinylsulfonylethyl)ether; and more preferred are one or more linear sulfonic acid esters selected from butane-2,3-diyl dimethanesulfonate, and pentafluorophenyl methanesulfonate.

The content of the S=O group-containing compound is preferably from 0.001 to 5% by mass in the nonaqueous electrolytic solution. Within the range, a sufficient film could be formed not growing excessively and the effect thereof for enhancing the electrochemical characteristics in a broad temperature range can be augmented. The content is more preferably at least 0.005% by mass, even more preferably at least 0.01% by mass, still more preferably at least 0.03% by mass in the nonaqueous electrolytic solution, and its upper limit is preferably at most 3% by mass, more preferably at most 1% by mass, even more preferably at most 0.7% by mass, most preferably at most 0.4% by mass.

[Electrolyte Salt]

As the electrolyte salt for use in the present invention, preferably mentioned are the following lithium salts and onium salts.

(Lithium Salt)

The lithium salt includes inorganic lithium salts, such as $LiPF_6$, $LiPO_2F_2$, $Li_2PO_3F$, $LiBF_4$, $LiClO_4$, $LiSO_3F$, etc.; linear fluoroalkyl group-having lithium salts, such as $LiN(SO_2F)_2$, $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; cyclic fluoroalkylene chain-having lithium salts, such as $(CF_2)_2(SO_2)_2NLi$, $(CF_2)_3(SO_2)_2NLi$, etc.; and lithium salts with an oxalate complex as the anion therein, such as lithium bis[oxalate- O,O']borate, lithium difluoro[oxalate-O,O']borate, lithium difluoro[oxalate-O,O']phosphate, lithium tetrafluoro[oxalate-O,O']phosphate, etc. One or more of these as compound may be used here.

Of those, preferred are one or more selected from $LiPF_6$, $LiPO_2F_2$, $Li_2PO_3F$, $LiBF_4$, $LiSO_3F$, $LiN(SO_2CF_3)_2$, $LiN(SO_2C_2F_6)_2$, $LiN(SO_2F)_2$, lithium difluorobis[oxalate-O,O']phosphate and lithium tetrafluoro[oxalate-O,O']phosphate; and more preferred are one or more selected from $LiPF_6$, $LiPO_2F_2$, $LiBF_4$, $LiN(SO_2CF_3)_2$, $LiN(SO_2F)_2$ and lithium difluorobis[oxalate-O,O']phosphate. The concentration of the lithium salt is preferably at least 0.3 M relative to the above-mentioned nonaqueous solvent, more preferably at least 0.7 M, even more preferably at least 1.1 M. The upper limit of the content is preferably at most 2.5 M, more preferably at most 2.0 M, even more preferably at most 1.6 M.

A preferred combination of these lithium salts to be contained in the nonaqueous electrolytic solution comprises $LiPF_6$ and contains at least one or more lithium salts selected from $LiPO_2F_2$, $LiBF_4$, $LiN(SO_2CF_3)_2$, $LiN(SO_2F)_2$ and lithium difluorobis[oxalate-O,O']phosphate. When the proportion of the lithium salt except $LiPF_6$ to be in the nonaqueous solvent is at least 0.001 M, then the electrolytic solution could readily exhibit the effect thereof of enhancing the electrochemical characteristics at high temperature, and when the content is at most 0.005 M, then the risk of depressing the effect of enhancing the electrochemical characteristics at high temperature would be low, and the range is therefore preferred. Preferably, the proportion is at least 0.01 M, more preferably at least 0.03 M, most preferably at least 0.04 M. The upper limit of the proportion is preferably at most 0.4 M, more preferably at most 0.2 M.

(Onium Salt)

Preferred examples of the onium salt are various salts of a combination of an onium cation and an anion mentioned below.

As the onium cation, preferably mentioned are one or more selected from a tetramethylammonium cation, an ethyltrimethylammonium cation, a diethyldimethylammonium cation, a triethylmethylammonium cation, a tetraethylammonium cation, an N,N-dimethylpyrrolidinium cation, an N-ethyl-N-methylpyrrolidinium cation, an N,N-diethylpyrrolidinium cation, a Spiro-(N,N')-bipyrrolidinium cation, an N,N'-dimethylimidazolinium cation, an N-ethyl-N'-methylimidazolinium cation, an N,N'-dimethylimidazolinium cation, an N,N'-dimethylimidazolinium cation, an N-ethyl-N'-methylimidazolinium cation, an N,N'-diethylimidazolinium cation.

Preferred examples of the anion include a $PF_6$ anion, a $BF_4$ anion, a $ClO_4$ anion, an $AsF_6$ anion, a $CF_3SO_3$ anion, an $N(CF_3SO_2)_2$ anion, an $N(C_2F_5SO_2)_2$ anion, etc.

One alone or two or more different types of these electrolyte salts may be used here either singly or as combined.

[Production of Nonaqueous Electrolytic Solution]

The nonaqueous electrolytic solution of the present invention may be produced, for example, by mixing the above-mentioned nonaqueous solvents, adding the above-mentioned electrolyte salt, and further adding thereto the cyclic sulfonic acid ester compound represented by the above-mentioned general formula (I) to the resulting nonaqueous electrolytic solution.

Preferably, the nonaqueous solvent to be used and the compound to be added to the nonaqueous electrolytic solution are previously purified to reduce as much as possible the content of impurities therein within a range not extremely detracting from the productivity.

The nonaqueous electrolytic solution of the present invention can be used in the first to fourth energy storage devices mentioned below, in which as the nonaqueous electrolyte, not only a liquid one but also a gelled one may be used. Further, the nonaqueous electrolytic solution of the present invention can also be used for solid polymer electrolytes. Especially preferably, the solution is used in the first energy storage device where a lithium salt is used as the electrolyte salt (that is, for lithium batteries), or in the fourth energy storage device (that is, for lithium ion capacitors); and more suitably, the solution is used for lithium batteries, even more preferably for lithium secondary batteries.

[First Energy Storage Device (Lithium Battery)]

The lithium battery in this specification means a generic name for a lithium primary battery and a lithium secondary battery. In this specification, the term, lithium secondary battery is used as a concept that includes so-called lithium ion secondary batteries. The lithium battery of the present invention comprises a positive electrode, a negative electrode, and the above-mentioned nonaqueous electrolytic solution of an electrolyte salt dissolved in a nonaqueous solvent. The other constitutive members, such as the positive electrode, the negative electrode and others than the nonaqueous electrolytic solution are not specifically defined for use herein.

For example, as the positive electrode active material for lithium secondary batteries, usable is a complex metal oxide of lithium and one or more selected from cobalt, manganese and nickel. One alone or two or more of these positive electrode active materials may be used here either singly or as combined.

The lithium complex metal oxide includes, for example, $LiCoO_2$, $LiMn_2O_4$, $LiNiO_2$, $LiCo_{1-x}Ni_xO_2$ ($0.01<x<1$) $LiCo_{1/3}Ni_{1/3}Mn_{1/3}O_2$, $LiNi_{1/2}Mn_{3/2}O_4$, $LiCo_{0.98}Mg_{0.02}O_2$, etc. Also usable here is a combination of $LiCoO_2$ and $LiMn_2O_4$, a combination of $LiCoO_2$ and $LiNiO_2$, or a combination of $LiMn_2O_4$ and $LiNiO_2$.

For improving the safety in overcharging and the cycle characteristics of the batteries, or for enabling the use thereof at a charge potential of 4.3 V or more, a part of the lithium complex metal oxide may be substituted with any other element. For example, a part of cobalt, manganese and nickel may be substituted with at least one or more elements of Sn, Mg, Fe, Ti, Al, Zr, Cr, V, Ga, Zn, Cu, Bi, Mo, La, etc.; or a part of O may be substituted with S or F; or the oxide may be coated with a compound containing any of such other elements.

Of those, preferred are lithium complex metal oxides, such as $LiCoO_2$, $LiMn_2O_4$ and $LiNiO_2$, with which the charge potential of the positive electrode in a fully-charged state could be 4.3 V or more based on Li; and more preferred are lithium complex metal oxides, such as solid solutions of $LiCo_{1-x}M_xO_2$ (where M is one or more elements selected from Sn, Mg, Fe, Ti, Al, Zr, Cr, V, Ga, Zn and Cu; $0.001 \leq x \leq 0.05$), $LiCo_{1/3}Ni_{1/3}Mn_{1/3}O_2$, $LiNi_{1/2}Mn_{3/2}O_4$, $Li_2MnO_3$ and $LiMO_2$ (where M is a transition metal, such as Co, Ni, Mn, Fe, etc.) that can be used at 4.4 V or more. When the lithium complex metal oxide capable of acting at a high charge voltage is used, then the electrochemical characteristics in use thereof in an especially broad temperature range may often worsen owing to the reaction of the oxide with the electrolytic solution in charging; however, in the lithium secondary battery of the present invention, the electrochemical characteristics can be prevented from worsening.

In particular, a battery with an Mn-containing positive electrode tends to have an increased resistance owing to the release of Mn ion from the positive electrode, and therefore in use in a broad temperature range, the electrochemical characteristics of the battery of the type tends to worsen. However, of the lithium secondary battery of the present invention, the electrochemical characteristics can be prevented from worsening and the battery is therefore preferred.

Further, lithium-containing olivine-type phosphates are also usable as the positive electrode active material. Especially preferred are lithium-containing olivine-type phosphates containing one or more selected from iron, cobalt, nickel and manganese. As their specific examples, there may be mentioned one or more selected from include $LiFePO_4$, $LiCoPO_4$, $LiNiPO_4$, and $LiMnPO_4$.

The lithium-containing olivine-type phosphates may be partly substituted with any other element. For example, a part of iron, cobalt, nickel and manganese therein may be substituted with one or more elements selected from Co, Mn, Ni, Mg, Al, B, Ti, V, Nb, Cu, Zn, Mo, Ca, Sr, W and Zr; or the phosphates may be coated with a compound containing any of these other elements or with a carbon material. Of those, preferred are $LiFePO_4$ and $LiMnPO_4$.

The lithium-containing olivine-type phosphate may be combined with, for example, the above-mentioned positive electrode active material.

For the positive electrode for lithium primary batteries, there are mentioned oxides or chalcogen compounds of one or more metal elements, such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_6$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds, such as $SO_2$, $SOCl_2$, etc.; carbon fluorides (graphite fluoride) represented by a general formula $(CF_x)_n$, etc. Of those, preferred are $MnO_2$, $V_2O_5$, fluorographite, etc.

The pH of the supernatant of a dispersion prepared by dispersing 10 g of the above-mentioned positive electrode active material in 100 ml of distilled water is preferably from 10.0 to 12.5, as the case readily brings about the effect of enhancing the electrochemical characteristics in a markedly broad temperature range. More preferably, the pH range is from 10.5 to 12.0.

In case where an element Ni is contained in the positive electrode, impurities, such as LiOH in the positive electrode active material may increase and the case is preferred as readily bringing about the effect of enhancing the electrochemical characteristics in a markedly broad temperature range. More preferably, the Ni atom concentration in the positive electrode active material is from 5 to 25 atomic %, even more preferably from 8 to 21 atomic %.

Not specifically defined, the electroconductive agent of the positive electrode may be any electron-conductive material not undergoing chemical change. For example, there may be mentioned graphites, such as natural graphite (flaky graphite, etc.), artificial graphite, etc.; and one or more carbon blacks selected from acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent, such as acetylene black, carbon black or the like, and with a binder, such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling-point solvent, such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 g/cm³, and for further increasing the capacity of the battery, the density is preferably at least 2 g/cm³, more preferably at least 3 g/cm³, even more preferably at least 3.6 g/cm³. The upper limit is preferably at most 4 g/cm³.

As the negative electrode active material for the lithium secondary battery, usable are one or more of lithium metal, lithium alloys, carbon materials capable of absorbing and releasing lithium [graphatizable carbon, non-graphatizable carbon where the lattice (002) spacing is at least 0.37 nm, graphite where the lattice (002) spacing is at most 0.34 nm, etc.], tin (elementary substance), tin compounds, silicon (elementary substance), silicon compounds, lithium titanate compounds, such as $Li_4Ti_5O_{12}$ and the like, either singly or as combined with two or more thereof.

Of those, more preferred is use of high-crystalline carbon materials, such as artificial graphite, natural graphite and the like, in view of the ability thereof to absorb and release lithium ions, and even more preferred is use of a carbon material having a graphite-type crystal structure where the lattice (002) spacing ($d_{002}$) is at most 0.340 nm (nanometers), especially from 0.335 to 0.337 nm.

In particular, preferred here is use of artificial graphite particles having a bulky structure where plural flattened graphite fine particles aggregate or bond together non-parallel to each other, or graphite particles produced through treatment of spheroidization of flaky natural graphite by imparting thereto repeated mechanical action, such as compression force, friction force, shear force or the like.

Preferably, the ratio of the peak intensity I (110) of the (110) plane of the graphite crystal obtained in X-ray diffractiometry of a negative electrode sheet as formed by pressing so that the density of the part except the collector of the negative electrode could be at least 1.5 g/cm³, to the peak intensity I (004) of the (004) plane thereof, I(110)/I (004) is at least 0.01, since the electrochemical characteristics of the battery can be enhanced in a markedly broad temperature range. More preferably, the ratio is at least 0.05, even more preferably at least 0.1. On the other hand, when too much processed, then the crystallinity may worsen and the discharge capacity of the battery may lower; and therefore, the upper limit of the peak intensity I(110)/I(004) is preferably at most 0.5, more preferably at most 0.3.

Preferably, the high-crystalline carbon material (core material) is coated with a different carbon material that is more low-crystalline than the core material, as further bettering the electrochemical characteristics in a broad temperature range. The crystallinity of the carbon material in coating may be confirmed through TEM.

When the high-crystalline carbon material is used, it may readily react with the nonaqueous electrolytic solution in charging to thereby worsen the electrochemical characteristics at low temperature or at high temperature owing to the increase in the interfacial resistance; however, in the lithium secondary battery of the present invention, the electrochemical characteristics in a broad range can be bettered.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of elementary substances, alloys, oxides, nitrides, sulfides, borides, alloys with lithium or the like; but preferred are any of elementary substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the battery capacity.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

The density of the part except the collector of the negative electrode may be generally at least 1.1 g/cm$^3$, and for further increasing the battery capacity, the density is preferably at least 1.5 g/cm$^3$, more preferably at least 1.7 g/cm$^3$. The upper limit is preferably at most 2 g/cm$^3$.

As the negative electrode active material for lithium primary batteries, usable are lithium metal or lithium alloys.

The structure of the lithium battery is not specifically defined. The battery may be a coin-type battery, a cylinder-type battery, a square-shaped battery, a laminate-type battery or the like, each having a single-layered or multi-layered separator.

The separator for the battery is not specifically defined, for which usable is a single-layer or laminate porous film of polyolefin, such as polypropylene, polyethylene or the like, as well as a woven fabric, a nonwoven fabric, etc.

The lithium secondary battery of the present invention has excellent electrochemical characteristics in a broad temperature range even when the final charging voltage is 4.2 V or more, especially 4.3 V or more, and further, the characteristics of the battery are still good even at 4.4 V or more. The final discharging voltage could be generally 2.8 V or more, further 2.5 V or more; however, the final discharging voltage of the lithium secondary battery of the present invention could be 2.0 V or more. The current value is not specifically defined, but in general, the battery is used within a range of from 0.1 to 30 C. The lithium battery of the present invention can be charged/discharged at −40 to 100° C., preferably at −10 to 80° C.

In the present invention, as a countermeasure against the increase in the internal pressure of the lithium battery, there may be employed a method of providing a safety valve in the battery cap or a method of forming a cutout in the battery component, such as the battery can, the gasket or the like. In addition, as a safety countermeasure against overcharging, a current cut-off mechanism capable of detecting the internal pressure of the battery to cut off the current may be provided in the battery cap.

[Second Energy Storage Device (Electric Double-Layer Capacitor)]

This is an energy storage device that stores energy by utilizing the electric double layer capacitance in the interface between the electrolytic solution and the electrode therein. One example of the present invention is an electric double layer capacitor. The most typical electrode active material to be used in the energy storage device is active carbon. The double layer capacitance increases almost in proportion to the surface area.

[Third Energy Storage Device]

This is an energy storage device that stores energy by utilizing the doping/dedoping reaction of the electrode therein. As the electrode active material for use in the energy storage device, there may be mentioned metal oxides, such as ruthenium oxide, iridium oxide, tungsten oxide, molybdenum oxide, copper oxide, etc.; π-conjugated polymers, such as polyacene, polythiophene derivatives, etc. The capacitor that uses the electrode active material of the type enables energy storage along with the doping/dedoping reaction at the electrode therein.

[Fourth Energy Storage Device (Lithium Ion Capacitor)]

This is an energy storage device that stores energy by utilizing the lithium ion intercalation into the carbon material, such as graphite or the like of the negative electrode therein. This may be referred to as a lithium ion capacitor (LIC). As the positive electrode, for example, there may be mentioned one that utilizes the electric double layer between the active carbon electrode and the electrolytic solution therein, or one that utilizes the doping/dedoping reaction of the π-conjugated polymer electrode therein. The electrolytic solution contains at least a lithium salt, such as LiPF$_6$ or the like.

[Cyclic Sulfonic Acid Ester Compound]

The novel compound of the invention, cyclic sulfonic acid ester compound is represented by the following general formula (II):

[Chem. 4]

(II)

(In the formula, R$^1$ and R$^2$ may be the same or different, each representing a hydrogen atom, an alkyl group having from 1 to 6 carbon atoms in which at least one hydrogen atom may be substituted with a halogen atom, or a halogen atom; L$^1$ represents a divalent hydrocarbon group of an alkylene group having 2 or 3 carbon atoms in which at least one hydrogen atom is substituted with OR$^6$, or a divalent hydrocarbon group of an alkylene group having 2 or 3 carbon atoms in which at least one methylene (CH$_2$) group is substituted with a group C(═O); R$^6$ represents a formyl group, an alkenylcarbonyl group having from 3 to 7 carbon atoms, an alkynylcarbonyl group having from 3 to 7 carbon atoms, an alkoxycarbonyl group having from 2 to 7 carbon atoms, an alkenyloxycarbonyl group having from 3 to 7 carbon atoms, an alkynyloxycarbonyl group having from 4 to 7 carbon atoms, an aryloxycarbonyl group having from 7 to 13 carbon atoms, a 2,2-dioxide-1,2-oxathiolan-4-yloxycarbonyl group, a 2,2-dioxide-1,2-oxathian-4-yloxycarbonyl group, a dialkylphosphoryl group having from 2 to 12 carbon atoms, an alkoxy(alkyl)phosphoryl group having from 2 to 12 carbon atoms, a dialkoxyphosphoryl group having from 2 to 12 carbon atoms, a group —S(O)—OR$^4$ or a group —C(O)CH$_2$P(O) (OR$^5$)$_2$; R$^4$ represents an alkyl group having from 1 to 6 carbon atoms, a 2,2-dioxide-1,2-oxathiolan-4-yl group, or a 2,2-dioxide-1,2-oxathian-4-yl group; $R^5$ represents an alkyl group having from 1 to 6 carbon atoms. Further, in $R^6$, at least one hydrogen atom may be substituted with a halogen atom, and 12 may be further substituted with any of an alkyl group having from 1 to 6 carbon atoms, a haloalkyl group having from 1 to 6 carbon atoms, or a halogen atom. However, when $L^1$ is a divalent hydrocarbon group of an alkylene group having 2 or 3 carbon atoms in which at least one methylene (CH$_2$) group is substituted with a group C(=O) then $R^1$ and $R^2$ are hydrogen atoms.)

In the general formula (II), the substituent $L^1$ represents a divalent hydrocarbon group of an alkylene group having 2 or 3 carbon atoms in which at least one hydrogen atom is substituted with OR$^6$, or a divalent hydrocarbon group of an alkylene group having 2 or 3 carbon atoms in which at least one methylene (CH$_2$) group is substituted with a group C(=O), and $R^6$ is as mentioned above. Of the substituent $R^6$, the alkenylcarbonyl group having from 3 to 7 carbon atoms, the alkynylcarbonyl group having from 3 to 7 carbon atoms, the alkoxycarbonyl group having from 2 to 7 carbon atoms, the alkenyloxycarbonyl group having from 3 to 7 carbon atoms, the alkynyloxycarbonyl group having from 4 to 7 carbon atoms, the aryloxycarbonyl group having from 7 to 13 carbon atoms, the 2,2-dioxide-1,2-oxathiolan-4-ylcarbonyl group, the 2,2-dioxide-1,2-oxathian-4-yloxycarbonyl group, the dialkylphosphoryl group having from 2 to 12 carbon atoms, the alkoxy(alkyl)phosphoryl group having from 2 to 12 carbon atoms, the dialkoxyphosphoryl group having from 2 to 12 carbon atoms, the group —S(O)—OR$^4$ and the group C(O)CH$_2$P(O) (OR$^5$)$_2$ have been described hereinabove in the above-mentioned general formula (I), and the description thereof is omitted in this section for evading redundant description. In this case, the substituents L and $R^3$ in the general formula (I) are read as the substituents $L^1$ and $R^6$ in the general formula (II).

In the general formula (II), the substituents $R^1$, $R^2$, $R^4$ and $R^5$ are the same as in the general formula (I).

The cyclic sulfonic acid ester compound of the present invention can be produced according to any of the following methods (a) to (d), to which, however, the compound production is not limited.

(a) A method of reacting a hydroxy cyclic sulfonic acid ester and a corresponding alkenylcarbonyl halide, alkoxycarbonyl halide, alkenyl oxycarbonyl halide, alkynyloxycarbonyl halide, aryloxycarbonyl halide, dialkylphosphoryl halide, alkoxy(alkyl)phosphoryl halide, dialkoxyphosphoryl halide or 2-(dialkoxyphosphoryl) acetic acid halide in the presence or absence of a solvent and in the presence or absence of a base (hereinafter this may be referred to as "method (a)").

(b) A method of reacting a hydroxy cyclic sulfonic acid ester and a carbonylating agent in the presence or absence of a solvent (hereinafter this may be referred to as "method (b)".

(c) A method of reacting a hydroxy cyclic sulfonic acid ester and a hydroxy compound and a thionyl halide corresponding thereto, in the presence or absence of a solvent and in the presence or absence of a base (hereinafter this may be referred to as "method (c)").

(d) A method of condensing a hydroxy cyclic sulfonic acid ester and a corresponding carboxylic acid compound in the presence or absence of a solvent and in the presence of an acid catalyst or a dehydrating agent (hereinafter this may be referred to as "method (d)").

[Method (a)]

The method (a) comprises reacting a hydroxy cyclic sulfonic acid ester and a corresponding alkenylcarbonyl halide, alkoxycarbonyl halide, alkenyloxycarbonyl halide, alkynyloxycarbonyl halide, aryloxycarbonyl halide, dialkylphosphoryl halide, alkoxy(alkyl)phosphoryl halide, dialkoxyphosphoryl halide or 2-(dialkoxyphosphoryl) acetic acid halide (hereinafter the compound may be referred to as "halide compound") in the presence or absence of a solvent and in the presence or absence of a base. The starting material, hydroxy cyclic sulfonic acid ester may be produced according to an already-existing method, for example, according to the method described in WO2011-016440.

For the reaction of the method (a), the amount of the halide compound to be used is preferably from 0.8 to 20 mols relative to one mol of the hydroxy cyclic sulfonic acid ester, more preferably from 0.9 to 10 mols, even more preferably from 1 to 5 mols.

The halide compound to be used in the method (a) includes acrylic acid chloride, methacrylic acid chloride, crotonic acid chloride, methyl chloroformate, ethyl chloroformate, vinyl chloroformate, 2-propenyl chloroformate, 2-propynyl chloroformate, phenyl chloroformate, 4-methylphenyl chloroformate, 4-fluorophenyl chloroformate, dimethylphosphoryl chloride, methoxy(methyl)phosphoryl chloride, dimethoxyphosphoryl chloride, diethoxyphosphoryl chloride, 2-(diethoxyphosphoryl)acetic acid chloride, etc.

The reaction of the method (a) may go on in the absence of a solvent, for which, however, a solvent inert to the reaction may be used. The solvent to be used includes aliphatic hydrocarbons, such as heptane, cyclohexane, etc.; halogenohydrocarbons, such as dichloromethane, dichloroethane, etc.; aromatic hydrocarbons, such as toluene, xylene, etc.; halogenoaromatic hydrocarbons, such as chlorobenzene, fluorobenzene, etc.; ethers, such as diisopropyl ether, dioxane, dimethoxyethane, tetrahydrofuran, etc.; esters, such as ethyl acetate, butyl acetate, dimethyl carbonate, diethyl carbonate, etc.; nitriles, such as acetonitrile, propionitrile, etc.; sulfoxides, such as dimethyl sulfoxide, sulfolane, etc.; amides, such as N,N-dimethylformamide, N,N-dimethylacetamide, etc.; and their mixtures. Of those, preferred are aliphatic or aromatic hydrocarbons and esters, such as heptane, cyclohexane, toluene, ethyl acetate, dimethyl carbonate, etc.

The amount of the solvent to be used is preferably from 0 to 30 parts by mass relative to one part by mass of the hydroxy cyclic sulfonic acid ester, more preferably from 1 to 10 parts by mass.

The reaction of the method (a) may go on in the absence of a base, but preferably a base is used as promoting the reaction. As the base, any of an inorganic base or an organic base is usable here.

The inorganic base includes potassium carbonate, sodium carbonate, calcium hydroxide and calcium oxide. The organic base includes linear or branched aliphatic tertiary amines, unsubstituted or substituted imidazoles, pyridines and pyrimidines. Of those, preferred are trialkylamines, such as trimethylamine, triethylamine, tripropylamine, tributylamine, diisopropylethylamine, etc.; and pyridines, such as pyridine, N,N-dimethylaminopyridine, etc.

The amount of the base to be used is preferably from 0.8 to 5 mols relative to 1 mol of the hydroxy cyclic sulfonic acid ester, more preferably from 1 to 3 mols, even more preferably from 1 to 1.5 mols.

For the reaction of the method (a), the lower limit of the reaction temperature is preferably not lower than −20° C., more preferably not lower than −10° C. from the viewpoint of not lowering the reactivity. The upper limit of the reaction temperature is preferably not higher than 80° C., more preferably not higher than 50° C. from the viewpoint of preventing side reaction and product decomposition.

The reaction time may be suitably changed depending on the reaction temperature and the reaction scale, but when the reaction time is too short, then unreacted matters would remain, and on the contrary, when the reaction time is too long, then the reaction product would decompose or side reaction would occur. Consequently, the reaction time is preferably from 0.1 to 12 hours, more preferably from 0.2 to 6 hours.

[Method (b)]

The method (b) comprises reacting a hydroxy cyclic sulfonic acid ester and a carbonylating agent in the presence or absence of a solvent.

In the reaction of the method (b), the amount of the carbonylating agent to be used is preferably from 0.4 to 5 mols relative to 1 mol of the hydroxy cyclic sulfonic acid ester, more preferably from 0.5 to 3 mols, even more preferably from 0.5 to 1 mol.

The carbonylating agent for use in the method (b) includes N,N'-carbonyldiimidazole, phenyl chloroformate, triphosgene, etc.

The reaction of the method (b) may go on in the absence of a solvent, for which, however, a solvent inert to the reaction may be used. As the solvent to be used here, there may be mentioned the aliphatic hydrocarbons, the halogenohydrocarbons, the aromatic hydrocarbons, the halogeno-aromatic hydrocarbons, the ethers, the nitriles, the sulfoxides and their mixtures described in the method (a). Of those, preferred are the aliphatic or aromatic hydrocarbons, such as heptane, cyclohexane, toluene and the like hardly miscible with water.

The amount of the solvent to be used is preferably from 0 to 30 parts by mass relative to one part by mass of the hydroxy cyclic sulfonic acid ester, more preferably from 1 to 10 parts by mass.

The reaction of the method (b) may go on in the absence of a base, but preferably a base is used as promoting the reaction. As the base, any of an inorganic base or an organic base is usable here.

The inorganic base includes potassium carbonate, sodium carbonate, calcium hydroxide and calcium oxide. The organic base includes linear or branched aliphatic tertiary amines, unsubstituted or substituted imidazoles, pyridines and pyrimidines. Of those, preferred are trialkylamines, such as trimethylamine, triethylamine, tripropylamine, tributylamine, diisopropylethylamine, etc.; and pyridines, such as pyridine, N,N-dimethylaminopyridine, etc.

The amount of the base to be used is preferably from 0.8 to 5 mols relative to 1 mol of the hydroxy cyclic sulfonic acid ester, more preferably from 1 to 3 mols, even more preferably from 1 to 1.5 mols.

For the reaction of the method (b), the lower limit of the reaction temperature is preferably not lower than −20° C., more preferably not lower than 0° C. from the viewpoint of not lowering the reactivity. The upper limit of the reaction temperature is preferably not higher than 80° C., more preferably not higher than 50° C. from the viewpoint of preventing side reaction and product decomposition.

The reaction time for the method (b) may be suitably changed depending on the reaction temperature and the reaction scale, but when the reaction time is too short, then unreacted matters would remain, and on the contrary, when the reaction time is too long, then the reaction product would decompose or side reaction would occur. Consequently, the reaction time is preferably from 0.1 to 24 hours, more preferably from 0.2 to 12 hours.

[Method (c)]

The method (c) comprises reacting a hydroxy cyclic sulfonic acid ester and a hydroxy compound and a thionyl halide corresponding thereto, in the presence or absence of a solvent and in the presence or absence of a base.

In the reaction of the method (c), the amount of the hydroxy compound to be used is preferably from 0.9 to 10 mols relative to 1 mol of the hydroxy cyclic sulfonic acid ester, more preferably from 1 to 5 mols, even more preferably from 1 to 3 mols.

The hydroxy compound to be used in the method (c) includes methanol, ethanol, allyl alcohol, propargyl alcohol, hydroxy cyclic sulfonic acid esters, etc.

In the reaction of the method (c), the amount of the thionyl halide to be used is preferably from 0.9 to 10 mols relative to 1 mol of the hydroxy cyclic sulfonic acid ester, more preferably from 1 to 5 mols, even more preferably from 1 to 3 mols.

The thionyl halide for use in the method (c) includes thionyl chloride, thionyl bromide, etc.

The reaction of the method (c) may go on in the absence of a solvent, for which, however, a solvent inert to the reaction may be used. As the solvent to be used here, there may be mentioned the aliphatic hydrocarbons, the halogenohydrocarbons, the aromatic hydrocarbons, the halogeno-aromatic hydrocarbons, the ethers, the nitriles, the sulfoxides and their mixtures described in the method (a). Of those, preferred are the aliphatic or aromatic hydrocarbons, such as heptane, cyclohexane, toluene and the like hardly miscible with water.

The amount of the solvent to be used is preferably from 0 to 30 parts by mass relative to one part by mass of the hydroxy cyclic sulfonic acid ester, more preferably from 1 to 10 parts by mass.

The reaction of the method (c) may go on in the absence of a base, but the presence of a base is preferred as promoting the reaction. As the base, any of an inorganic base or an organic base is employable here.

The inorganic base includes potassium carbonate, sodium carbonate, calcium hydroxide and calcium oxide. The organic base includes linear or branched aliphatic tertiary amines, unsubstituted or substituted imidazoles, pyridines and pyrimidines. Of those, preferred are trialkylamines, such as trimethylamine, triethylamine, tripropylamine, tributylamine, diisopropylethylamine, etc.; and pyridines, such as pyridine, N,N-dimethylaminopyridine, etc.

The amount of the base to be used is preferably from 0.8 to 5 mols relative to 1 mol of the hydroxy cyclic sulfonic acid ester, more preferably from 1 to 3 mols, even more preferably from 1 to 1.5 mols.

For the reaction of the method (c), the lower limit of the reaction temperature is preferably not lower than −20° C., more preferably not lower than −10° C. from the viewpoint of not lowering the reactivity. The upper limit of the reaction temperature is preferably not higher than 80° C., more preferably not higher than 50° C. from the viewpoint of preventing side reaction and product decomposition.

The reaction time for the method (c) may be suitably changed depending on the reaction temperature and the reaction scale, but when the reaction time is too short, then unreacted matters would remain, and on the contrary, when the reaction time is too long, then the reaction product would decompose or side reaction would occur. Consequently, the reaction time is preferably from 0.1 to 24 hours, more preferably from 0.2 to 12 hours.

[Method (d)]

The method (d) comprises condensing a hydroxy cyclic sulfonic acid ester and a corresponding carboxylic acid compound in the presence or absence of a solvent and in the presence of an acid catalyst or a dehydrating agent.

In the reaction of the method (d), the amount of the carboxylic acid to be used is preferably from 0.8 to 20 mols relative to 1 mol of the hydroxy cyclic sulfonic acid ester, more preferably from 0.9 to 10 mols, even more preferably from 1 to 5 mols.

The carboxylic acid compound to be used in the method (d) includes formic acid, acrylic acid, methacrylic acid, crotonic acid, propiolic acid, 2-(diethoxyphosphoryl)acetic acid.

The reaction of the method (d) may go on in the absence of a solvent, for which, however, a solvent inert to the reaction may be used. As the solvent to be used here, there may be mentioned the aliphatic hydrocarbons, the halogenohydrocarbons, the aromatic hydrocarbons, the halogenoaromatic hydrocarbons, the ethers, the nitriles, the sulfoxides and their mixtures described in the method (a). Of those, preferred are the aliphatic or aromatic hydrocarbons, such as heptane, cyclohexane, toluene, etc.

The amount of the solvent to be used is preferably from 0 to 30 parts by mass relative to one part by mass of the carboxylic acid compound, more preferably from 1 to 10 parts by mass.

In case where an acid catalyst is used in the method (d), the acid catalyst usable therein includes mineral acids, such as sulfuric acid, phosphoric acid, etc.; sulfonic acids, such as paratoluenesulfonic acid, methanesulfonic acid, trifluoromethanesulfonic acid, etc.; Lewis acids, such as trifluoroboric acid, tetraisopropoxytitanium, etc.; solid acids, such as zeolite, acid resin, etc.; and their mixtures. Of those, preferred are sulfonic acids, such as paratoluenesulfonic acid, methanesulfonic acid, trifluoromethanesulfonic acid, etc.; and Lewis acids, such as tetraisopropoxytitanium, etc. The amount of the catalyst to be used is preferably from 0.001 to 5 mols relative to 1 mol of the carboxylic acid from the viewpoint of preventing side reaction, more preferably from 0.01 to 1 mol, even more preferably from 0.01 to 0.3 mols.

In case where a dehydrating agent is used, usable as the dehydrating agent are one or more selected from dicyclohexylcarbodiimide, 1-ethyl-3-(3-dimethylaminopropyl)carbodiimide hydrochloride (WSC), N,N'-carbonyldiimidazole, di-2-pyridyl carbonate, phenyl dichlorophosphate, a mixture of ethyl diethylazodicarboxylate and triphenyl phosphine, etc. The amount of the dehydrating agent to be used is preferably from 0.8 to 10 mols relative to 1 mol of the hydroxy cyclic sulfonic acid ester, more preferably from 0.9 to 5 mols, even more preferably from 1 to 3 mols.

In the reaction of the method (d) where an acid catalyst is used, the lower limit of the reaction temperature is preferably not lower than 0° C., but from the viewpoint of not lowering the reactivity, the reaction temperature is more preferably not lower than 20° C. Also from the viewpoint of preventing side reaction and product decomposition, the upper limit of the reaction temperature is preferably not higher than 200° C., more preferably not higher than 150° C.

The lower limit of the reaction temperature in the case of using a dehydrating agent is preferably not lower than −20° C., but from the viewpoint of not lowering the reactivity, the reaction temperature is more preferably not lower than 0° C. Also from the viewpoint of preventing side reaction and product decomposition, the upper limit of the reaction temperature is preferably not higher than 100° C., more preferably not higher than 50° C.

The reaction time may be suitably changed depending on the reaction temperature and the reaction scale, but when the reaction time is too short, then unreacted matters would remain, and on the contrary, when the reaction time is too long, then the reaction product would decompose or side react ion would occur. Consequently, the reaction time is preferably from 0.1 to 24 hours, more preferably from 0.2 to 12 hours.

EXAMPLES

Synthesis Examples of cyclic sulfonic acid ester compounds and Examples of electrolytic solutions are shown below; however, the present invention is not limited to these Synthesis Examples and Examples.

Synthesis Example 1

Synthesis of 2,2-dioxide-1,2-oxathiolan-4-yl methyl carbonate (synthetic compound 1)

1.99 g (14.4 mmol) of 4-hydroxy-1,2-oxathiolane-2,2-dioxide and 2.20 g (21.7 mmol) of triethylamine were dissolved in 50 mL of ethyl acetate, and cooled to 10° C. 2.05 g (21.7 mmol) of methyl chloroformate was dropwise added to the solution at 10 to 15° C., taking 15 minutes, and then stirred at room temperature for 1 hour. The disappearance of the starting materials was confirmed through TLC, then the reaction liquid was washed with water, then processed for liquid-liquid separation, and the organic layer was concentrated. The residue was purified through silica gel column chromatography (ethyl acetate/hexane=3/2 for elution) to give 2.12 g (yield 75%) of the intended 2,2-dioxide-1,2-oxathiolan-4-yl methyl carbonate.

The obtained 2,2-dioxide-1,2-oxathiolan-4-yl methyl carbonate was analyzed through $^1$H-NMR to confirm the structure thereof. The results are shown below.

$^1$H-NMR (300 MHz, CDCl$_3$): δ=5.58-5.52 (m, 1H), 4.68-4.61 (m, 1H), 4.56-4.51 (m, 1H), 3.89 (s, 3H), 3.69-3.62 (m, 1H), 3.44-3.38 (m, 1H)

Synthesis Example 2

Synthesis of 2,2-dioxide-1,2-oxathiolan-4-yl vinyl carbonate (synthetic compound 2)

The intended compound was obtained according to the same method as in Synthesis Example 1, for which, however, vinyl chloroformate was used in place of methyl chloroformate.

The obtained 2,2-dioxide-1,2-oxathiolan-4-yl vinyl carbonate was analyzed through $^1$H-NMR to confirm the structure thereof. The results are shown below.

$^1$H-NMR (300 MHz, CDCl$_3$): δ=7.06-6.99 (m, 1H), 5.64-5.58 (m, 1H), 5.04-4.99 (m, 1H), 4.72-4.65 (m, 2H), 4.59-4.54 (m, 1H), 3.72-3.64 (m, 1H), 3.48-3.42 (m, 1H)

Synthesis Example 3

Synthesis of bis(2,2-dioxide-1,2-oxathiolan-4-yl) sulfite (synthetic compound 3)

3.00 g (21.7 mmol) of 4-hydroxy-1,2-dioxathiolane-2,2-dioxide and 2.19 g (21.7 mmol) of triethylamine were dissolved in 30 mL of ethyl acetate. With cooling with ice, 1.28 g (10.8 mmol) of thionyl chloride was added thereto, taking 10 minutes, and then stirred at room temperature for 30 minutes. After the reaction, triethylamine hydrochloride was removed through filtration, and the filtrate was concentrated. The resulting residue was purified through silica gel column chromatography (ethyl acetate/hexane=1/1 for elution) to give 1.11 g (yield 32%) of bis(2,2-dioxide-1,2-oxathiolan-4-yl) sulfite The obtained bis(2,2-dioxide-1,2-oxathiolan-4-yl) sulfite was analyzed through $^1$H-NMR to confirm the structure thereof. The results are shown below.

$^1$H-NMR (300 MHz, CDCl$_3$): δ=5.65-5.59 (m, 2H), 4.68-4.66 (m, 2H), 4.49-4.46 (m, 2H), 3.66-3.59 (m, 2H), 3.32-3.30 (m, 2H)

Synthesis Example 4

Synthesis of 2,2-dioxide-1,2-oxathiolan-4-yl 2-(diethoxyphosphoryl)acetate (synthetic compound 4)

0.92 g (6.7 mmol) of 4-hydroxy-1,2-oxathiolane-2,2-dioxide and 1.31 g (6.7 mmol) of 2-(diethoxyphosphoryl)acetic acid were dissolved in 20 mL of methylene chloride, and cooled to 10° C. To the solution, dropwise added was a solution prepared by dissolving 1.34 g (7.0 mmol) of 1-ethyl-3-(3-dimethylaminopropyl) carbodiimide hydrochloride in 10 mL of methylene chloride, at 10 to 15° C. taking 15 minutes, and then stirred at room temperature for 1 hour. The disappearance of the starting materials was confirmed through TLC, and then the reaction liquid was washed with water and processed for liquid-liquid separation, and the organic layer was concentrated. The residue was purified through silica gel column chromatography (ethyl acetate/hexane=1/1 for elution) to give 2.00 g (yield 95%) of the intended 2,2-dioxide-1,2-oxathiolan-4-yl 2-(diethoxyphosphoryl)acetate.

The obtained 2,2-dioxide-1,2-oxathiolan-4-yl 2-(diethoxyphosphoryl)acetate was analyzed through $^1$H-NMR to confirm the structure thereof. The results are shown below.

$^1$H-NMR (300 MHz, CDCl$_3$): δ=5.71-5.68 (m, 1H), 4.67-4.62 (m, 1H), 4.53-4.52 (m, 1H), 4.24-4.14 (m, 4H), 3.68-3.61 (m, 1H), 3.41-3.35 (m, 1H), 3.04 (d, 2H, J=21.7 Hz), 1.39-1.34 (m, 6H)

Synthesis Example 5

Synthesis of 2,2-dioxide-1,2-oxathiolan-4-yl acrylate (synthetic compound 5)

3.00 g (21.7 mmol) of 4-hydroxy-1,2-oxathiolane-2,2-dioxide and 3.29 g (32.5 mmol) of triethylamine were dissolved in 50 mL of ethyl acetate, and cooled to 10° C. 2.93 g (32.5 mmol) of acrylic acid chloride was dropwise added was to the solution at 10 to 15° C., taking 15 minutes, and then stirred at room temperature for 1 hour. The disappearance of the starting materials was confirmed through TLC, and then the reaction liquid was washed with water and processed for liquid-liquid separation, and the organic layer was concentrated. The residue was purified through silica gel column chromatography (ethyl acetate/hexane=3/2 for elution) to give 1.93 g (yield 460) of the intended 2,2-dioxide-1,2-oxathiolan-4-yl acrylate.

The obtained 2,2-dioxide-1,2-oxathiolan-4-yl acrylate was analyzed through $^1$H-NMR to confirm the structure thereof. The results are shown below.

$^1$H-NMR (300 MHz, CDCl$_3$): δ=6.55-6.38 (m, 1H), 6.21-5.85 (m, 2H), 5.74-5.65 (m, 1H), 4.71-4.63 (m, 1H), 4.53-4.43 (m, 1H), 3.71-3.60 (m, 1H), 3.42-3.34 (m, 1H)

Synthesis Example 6

Synthesis of 2,2-dioxide-1,2-oxathiolan-4-yl methacrylate (synthetic compound 6)

The intended compound was obtained ac cording to the same method as in Synthesis Example 5, for which, however, methacrylic acid chloride was used in place of acrylic acid chloride.

The obtained 2,2-dioxide-1,2-oxathiolan-4-yl methacrylate was analyzed through $^1$H-NMR to confirm the structure thereof. The results are shown below.

$^1$H-NMR (300 MHz, CDCl$_3$): δ=6.23-6.22 (dd, 1H, J=1.2, 1.0 Hz), 5.73-5.72 (dd, 1H, J=1.2, 1.0H), 5.71-5.67 (m, 1H), 4.72-4.66 (m, 1H), 4.54-4.50 (m, 1H), 3.70-3.62 (m, 1H), 3.41-3.30 (m, 1H), 1.97-1.96 (dd, 3H, J=1.2, 1.0 Hz)

Synthesis Example 7

Synthesis of 1,2-oxathiolan-4-one 2,2-dioxide (synthetic compound 7)

2.91 g (13.5 mmol) of pyridinium chlorochromate was suspended in 30 ml of anhydrous methylene chloride, and with stirring, 1.24 g (9.0 mmol) of 4-hydroxy-1,2-oxathiolane-2,2-dioxide dissolved in 30 mL of ethyl acetate was added thereto, and stirred at room temperature for 1 hour. 30 ml of ethyl acetate was added, the supernatant was removed, and the black residue was washed three times with 10 mL of ethyl acetate. The ethyl acetate layers were combined and concentrated. The residue was purified through silica gel column chromatography (ethyl acetate/hexane=3/2 for elution) to give 0.30 g (yield 250) of the intended 1,2-oxathiolan-4-one 2,2-dioxide.

The obtained 1,2-oxathiolan-4-one 2,2-dioxide was analyzed through $^1$H-NMR to confirm the structure thereof. The results are shown below.

$^1$H-NMR (300 MHz, CDCl$_3$): δ=4.82 (d, 2H, J=0.5 Hz), 3.86 (d, 2H, J=0.5 Hz)

Synthesis Example 8

Synthesis of 2,2-dioxide-1,2-oxathiolan-4-yl diethylphosphate (synthetic compound 8)

3.00 g (21.7 mmol) of 4-hydroxy-1,2-oxathiolane-2,2-dioxide, 2.63 g (26.0 mmol) of triethylamine and 0.027 g (0.22 mmol) of N,N-dimethyl-4-aminopyridine were dissolved in 50 mL of ethyl acetate, and cooled to 10° C. 4.12 g (23.9 mmol) of diethyl chlorophosphate was dropwise added to the solution at 10 to 15° C., taking 15 minutes, and then stirred at room temperature for 1 hour. The disappearance of the starting materials was confirmed through TLC, then the reaction liquid was washed with water, and processed for liquid-liquid separation, and the organic layer was concentrated. The residue was purified through silica gel column chromatography (ethyl acetate/hexane=2/1 for elution) to give 1.49 g (yield 38%) of the intended 2,2-dioxide-1,2-oxathiolan-4-yl diethylphosphate.

The obtained 2,2-dioxide-1,2-oxathiolan-4-yl diethylphosphate was analyzed through $^1$H-NMR to confirm the structure thereof. The results are shown below.

$^1$H-NMR (400 MHz, CDCl$_3$): δ=5.40-5.33 (m, 1H), 4.62-4.59 (m, 2H), 4.22-4.10 (m, 4H), 3.63-3.51 (m, 2H), 1.43-1.33 (m, 6H)

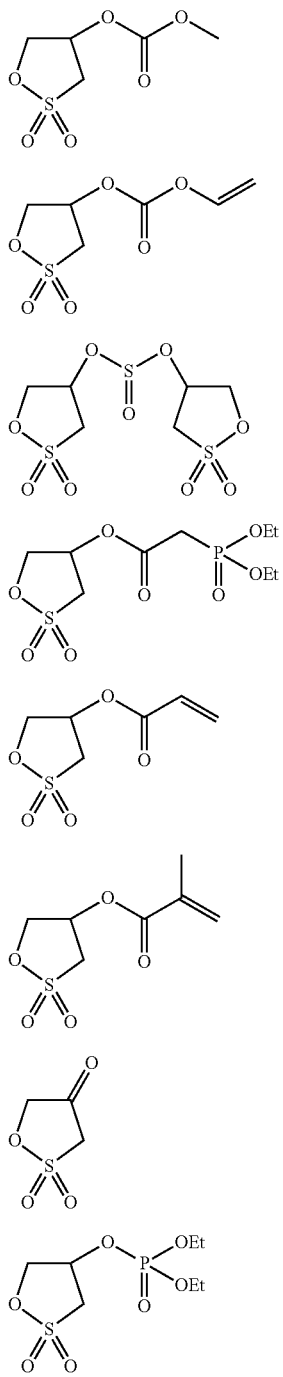

Synthetic Compound 1

Synthetic Compound 2

Synthetic Compound 3

Synthetic Compound 4

Synthetic Compound 5

Synthetic Compound 6

Synthetic Compound 7

Synthetic Compound 8

Examples 1 to 32, Comparative Examples 1 and 2

Production of Lithium Ion Secondary Battery

94% by mass of LiNi$_{1/3}$Mn$_{1/3}$Co$_{1/3}$O$_2$ (positive electrode active material, the pH of the supernatant of 10 g of the positive electrode active material dispersed in 100 ml of distilled water was 10.8) and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and blanked into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) was added to and mixed in a solution previously prepared by dissolving 5. % by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.5 g/cm$^3$. The electrode sheet was analyzed through X-ray diffractiometry, and the ratio of the peak intensity I(110) of the (110) plane of the graphite crystal to the peak intensity I(004) of the (004) plane thereof [I(110)/I(004)] was 0.1. The positive electrode sheet, a porous polyethylene film separator and the negative electrode sheet were laminated in that order, and the non-aqueous electrolytic solution having the composition shown in Table 1 and 2 was added thereto to construct a 2032 coin-type battery.

[Evaluation of Low-Temperature Characteristics after High-Temperature Charging Storage]

<Initial Discharge Capacity>

In a thermostatic chamber kept at 25° C., the coin-type battery produced according to the above-mentioned method was charged up to a final voltage of 4.2 V for 3 hours with a constant current of 1 C and under a constant voltage, then the temperature of the thermostatic chamber was lowered to 0° C., and the battery was discharged under a constant current of 1 C to a final voltage of 2.75 V. The initial discharge capacity at 0° C. was measured.

<High-Temperature Charging Storage Test>

Next, in a thermostatic chamber at 85° C., the coin-type battery was charged up to a final voltage of 4.2 V for 3 hours with a constant current of 1 C and under a constant voltage, and then stored for 3 days while kept at 4.2 V. Subsequently, this was put in a thermostatic chamber at 25° C., and once discharged under a constant current of 1 C to a final voltage of 2.75 V.

<Discharge Capacity after High-Temperature Charging Storage>

Further after that, the discharge capacity at 0° C. after high-temperature charging storage was measured in the same manner as that for the measurement of the initial discharge capacity.

<Low-Temperature Characteristics after High-Temperature Charging Storage>

The low-temperature characteristics after high-temperature charging storage were determined based on the 0° C. discharge capacity retention rate mentioned below.

0° C. Discharge Capacity Retention Rate at 0° C. after high-temperature charging storage (%)=(discharge capacity at 0° C. after high-temperature charging storage/initial discharge capacity at 0° C.)×100.

The battery characteristics are shown in Tables 1 and 2.

TABLE 1

| | Composition of Nonaqueous Electrolytic Solution (ratio by volume of solvents) | Cyclic Sulfonic Acid Ester Compound | | 0° C. Discharge Capacity Retention Rate after 85° C. high-temperature charging storage (%) |
|---|---|---|---|---|
| | Composition of Electrolyte Salt | Compound | Amount Added (content in nonaqueous electrolytic solution (wt %)) | |
| Example 1 | 1.2 M LiPF6 EC/DMC/MEC (30/45/25) | 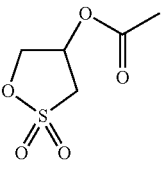 | 1 | 74 |
| Example 2 | 1.2 M LiPF6 EC/FEC/DMC/MEC (29/1/45/25) | 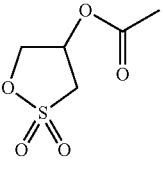 | 0.01 | 72 |
| Example 3 | 1.2 M LiPF6 EC/FEC/DMC/MEC (29/1/45/25) | 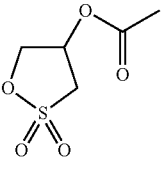 | 1 | 80 |
| Example 4 | 1.2 M LiPF6 EC/FEC/DMC/MEC (29/1/45/25) | 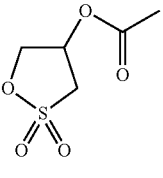 | 3 | 78 |
| Example 5 | 1.2 M LiPF6 EC/FEC/DMC/MEC (29/1/45/25) | 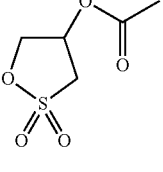 | 7 | 75 |
| Example 6 | 1.2 M LiPF6 EC/FEC/DMC/MEC (29/1/45/25) | 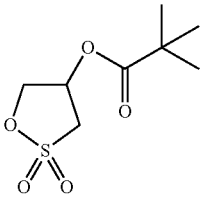 | 1 | 83 |
| Example 7 | 1.2 M LiPF6 EC/FEC/DMC/MEC (29/1/45/25) | 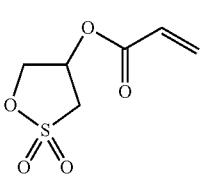 | 1 | 81 |
| Example 8 | 1.2 M LiPF6 EC/FEC/DMC/MEC (29/1/45/25) | 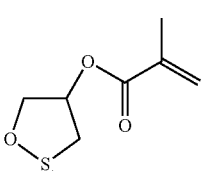 | 1 | 82 |

TABLE 1-continued

| | Composition of Electrolyte Salt Composition of Nonaqueous Electrolytic Solution (ratio by volume of solvents) | Cyclic Sulfonic Acid Ester Compound | | 0° C. Discharge Capacity |
|---|---|---|---|---|
| | | Compound | Amount Added (content in nonaqueous electrolytic solution (wt %)) | Retention Rate after 85° C. high-temperature charging storage (%) |
| Example 9 | 1.2 M LiPF6 EC/FEC/DMC/MEC (29/1/45/25) | 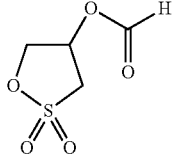 | 1 | 79 |
| Example 10 | 1.2 M LiPF6 EC/FEC/DMC/MEC (29/1/45/25) | 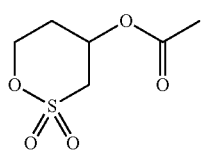 | 1 | 79 |
| Example 11 | 1.2 M LiPF6 EC/FEC/DMC/MEC (29/1/45/25) | 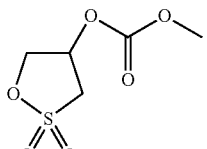 | 1 | 78 |
| Example 12 | 1.2 M LiPF6 EC/FEC/DMC/MEC (29/1/45/25) | 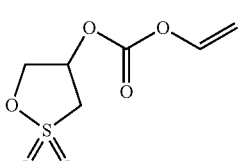 | 1 | 80 |
| Example 13 | 1.2 M LiPF6 EC/FEC/DMC/MEC (29/1/45/25) | 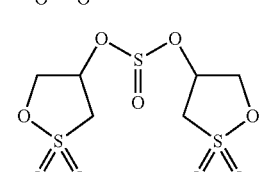 | 1 | 81 |
| Example 14 | 1.2 M LiPF6 EC/FEC/DMC/MEC (29/1/45/25) | 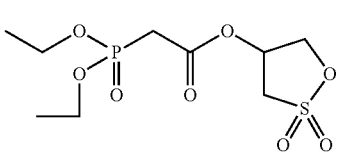 [SMILES: CCOP(=O)(CC(=O)OC1COS(=O)(=O)C1)OCC] | 1 | 78 |
| Example 15 | 1.2 M LiPF6 EC/FEC/DMC/MEC (29/1/45/25) | 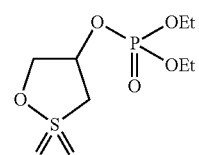 | 1 | 76 |
| Example 16 | 1.2 M LiPF6 + 0.05 M LiN(SO2CF3)2 PC/FEC/VC/DMC/MEC (18/10/2/45/25) | 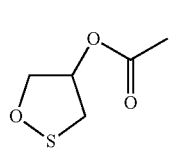 | 1 | 82 |
| Example 17 | 1.2 M LiPF6 + 0.05 M LiN(SO2CF3)2 PC/FEC/VC/DMC/MEC (18/10/2/45/25) +adiponitrile (1 wt %) | 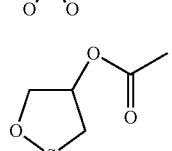 | 1 | 84 |

TABLE 1-continued

| | Composition of Electrolyte Salt Composition of Nonaqueous Electrolytic Solution (ratio by volume of solvents) | Cyclic Sulfonic Acid Ester Compound Compound | Amount Added (content in nonaqueous electrolytic solution (wt %)) | 0° C. Discharge Capacity Retention Rate after 85° C. high-temperature charging storage (%) |
|---|---|---|---|---|
| Example 18 | 1.2 M LiPF6 + 0.05 M LiN(SO2CF3)2 PC/FEC/VC/DMC/MEC (18/10/2/45/25) +1,3-propanesultone (1 wt %) | 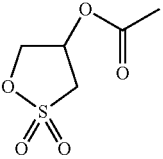 | 1 | 85 |
| Example 19 | 1.2 M LiPF6 + 0.05 M LiN(SO2CF3)2 PC/FEC/VC/DMC/MEC (18/10/2/45/25) +2,4-butanesultone (1 wt %) | 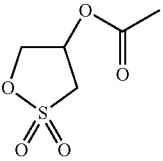 | 1 | 86 |
| Example 20 | 1.2 M LiPF6 + 0.05 M LiN(SO2CF3)2 PC/FEC/VC/DMC/MEC (18/10/2/45/25) +2-butyne-1,4-diyl-dimethanesulfonate (1 wt %) | 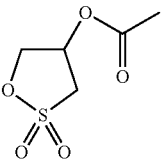 | 1 | 86 |
| Example 21 | .2 M LiPF6 + 0.05 M LiN(SO2CF3)2 PC/FEC/VC/DMC/MEC (18/10/2/45/25) +di(2-propynyl) oxalate (0.5 wt %) | 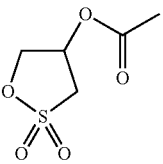 | 1 | 86 |
| Example 22 | 1.2 M LiPF6 + 0.05 M LiPF2(C2O4)2 PC/FEC/VC/DMC/MEC (18/10/2/45/25) | 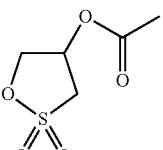 | 1 | 85 |
| Comparative Example 1 | 1.2 M LiPF6 EC/FEC/DMC/MEC (29/1/45/25) | none | — | 63 |
| Comparative Example 2 | 1.2 M LiPF6 EC/FEC/DMC/MEC (29/1/45/25) | 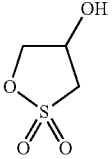 | 1 | 67 |

TABLE 2

| | Composition of Electrolyte Salt Composition of Nonaqueous Electrolytic Solution (ratio by volume of solvents) | Cyclic Sulfonic Acid Ester Compound | | 0° C. Discharge Capacity Retention Rate after 85° C. high-temperature charging storage (%) |
|---|---|---|---|---|
| | | Compound | Amount Added (content in nonaqueous electrolytic solution (wt %)) | |
| Example 23 | 1.2 M LiPF6 EC/FEC/DMC/MEC (29/1/45/25) | 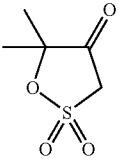 | 1 | 78 |
| Example 24 | 1.2 M LiPF6 EC/FEC/DMC/MEC (29/1/45/25) | 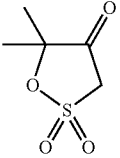 | 4 | 76 |
| Example 25 | 1.2 M LiPF6 EC/FEC/DMC/MEC (29/1/45/25) | 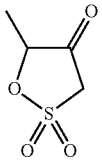 | 1 | 76 |
| Example 26 | 1.2 M LiPF6 EC/FEC/DMC/MEC (29/1/45/25) | 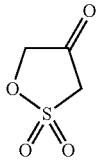 | 1 | 74 |
| Example 27 | 1.2 M LiPF6 EC/FEC/DMC/MEC (29/1/45/25) | 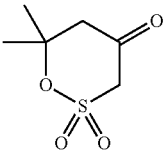 | 1 | 77 |
| Example 28 | 1.2 M LiPF6 + 0.05 M LiN(SO2CF3)2 PC/FEC/VC/DMC/MEC (18/10/2/45/25) | 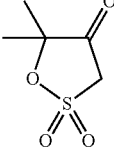 | 1 | 81 |
| Example 29 | 1.2 M LiPF6 + 0.05 M LiN(SO2CF3)2 PC/FEC/VC/DMC/MEC (18/10/2/45/25) +adiponitrile (1 wt %) | 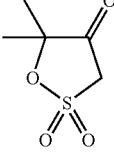 | 1 | 83 |
| Example 30 | 1.2 M LiPF6 + 0.05 M LiN(SO2CF3)2 PC/FEC/VC/DMC/MEC (18/10/2/45/25) +1,3-propanesultone (1 wt %) | 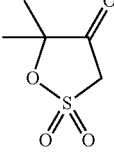 | 1 | 84 |

TABLE 2-continued

| | Composition of Electrolyte Salt / Composition of Nonaqueous Electrolytic Solution (ratio by volume of solvents) | Cyclic Sulfonic Acid Ester Compound / Compound | Amount Added (content in nonaqueous electrolytic solution (wt %)) | 0° C. Discharge Capacity Retention Rate after 85° C. high-temperature charging storage (%) |
|---|---|---|---|---|
| Example 31 | 1.2 M LiPF6 + 0.05 M LiN(SO2CF3)2 PC/FEC/VC/DMC/MEC (18/10/2/45/25) +2-butyne-1,4-diyl-dimethanesulfonate (1 wt %) | (structure) | 1 | 85 |
| Example 32 | 1.2 M LiPF6 + 0.05 M LiPF2(C2O4)2 PC/FEC/VC/DMC/MEC (18/10/2/45/25) | (structure) | 1 | 83 |
| Comparative Example 1 | 1.2 M LiPF6 EC/FEC/DMC/MEC (29/1/45/25) | none | — | 63 |

Examples 33 and 34, Comparative Example 3

A negative electrode sheet was produced, using silicon (elementary substance) (negative electrode active material) in place of the negative electrode active material used in Example 3 and Comparative Example 1. Precisely, 80% by mass of silicon (elementary substance) and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin-type batteries were produced and evaluated in the same manner as in Example 3 and Comparative Example 1, except that the negative electrode sheet produced herein was used. The results are shown in Table 3.

TABLE 3

| | Composition of Electrolyte Salt / Composition of Nonaqueous Electrolytic Solution (ratio by volume of solvents) | Cyclic Sulfonic Acid Ester Compound / Compound | Amount Added (content in nonaqueous electrolytic solution (wt %)) | 0° C. Discharge Capacity Retention Rate after 85° C. high-temperature charging storage (%) |
|---|---|---|---|---|
| Example 33 | 1.2 M LiPF6 EC/FEC/DMC/MEC (29/1/45/25) | (structure) | 1 | 64 |
| Example 34 | 1.2 M LiPF6 EC/FEC/DMC/MEC (29/1/45/25) | (structure) | 1 | 62 |
| Comparative Example 3 | 1.2 M LiPF6 EC/FEC/DMC/MEC (29/1/45/25) | none | — | 47 |

Examples 35 and 36, Comparative Example 4

A positive electrode sheet was produced by changing the positive electrode active material used in Example 3 and Comparative Example 1 to LiFePO₄ (positive electrode active material) coated with amorphous carbon. Concretely, 90% by mass of LiFePO₄ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet. Coin-type batteries were produced and evaluated in the same manner as in Example 3 and Comparative Example 1, except that the positive electrode sheet thus produced herein was used and that, in battery evaluation, the final charging voltage was changed to 3.6 V and the final discharging voltage was changed to 2.0 V. The results are shown in Table 4.

trochemical characteristics in a broad temperature range. In particular, when the nonaqueous electrolytic solution is used for energy storage devices, such as lithium secondary batteries and the like to be mounted on hybrid electric vehicles, plug-in hybrid electric vehicles, battery electric vehicles, etc., there can be obtained energy storage devices of which the electrochemical characteristics are hardly worsened in a broad temperature range.

TABLE 4

| | Composition of Electrolyte Salt | Cyclic Sulfonic Acid Ester Compound | | 0° C. Discharge Capacity |
|---|---|---|---|---|
| | Composition of Nonaqueous Electrolytic Solution (ratio by volume of solvents) | Compound | Amount Added (content in nonaqueous electrolytic solution (wt %)) | Retention Rate after 85° C. high-temperature charging storage (%) |
| Example 35 | 1.2 M LiPF6 EC/FEC/DMC/MEC (29/1/45/25) | | 1 | 79 |
| Example 36 | 1.2 M LiPF6 EC/FEC/DMC/MEC (29/1/45/25) | 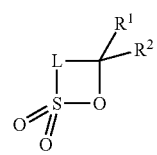 | 1 | 77 |
| Comparative Example 4 | 1.2 M LiPF6 EC/FEC/DMC/MEC (29/1/45/25) | none | — | 60 |

The lithium secondary batteries of Examples 1 to 32 were all remarkably bettered in point of the electrochemical characteristics thereof in a broad temperature range, as compared with the lithium secondary battery of Comparative Example 1 to which the cyclic sulfonic acid ester compound was not added to the nonaqueous electrolytic solution of the invention and that of Comparative Example 2 to which hydroxypropanesultone described in PTL 1 was added. From the above, it has been clarified that the advantageous effect of the present invention is peculiar to the nonaqueous electrolytic solution of an electrolyte salt dissolved in a nonaqueous solvent that contains from 0.001 to 10% by mass of the cyclic sulfonic acid ester compound of the invention.

In addition, from comparison of Examples 33 and 34 with Comparative Example 3, and from comparison of Examples 35 and 36 with Comparative Example 4, the same advantageous effect is seen in the case where silicon (elementary substance) was used as the negative electrode and in the case where a lithium-containing olivine-type iron phosphate was used as the positive electrode. Accordingly, it is obvious that the advantageous effect of the present invention does not depend on any specific positive electrode or negative electrode.

Further, the nonaqueous electrolytic solution of the present invention has an effect of improving the discharge characteristics of lithium primary batteries in a broad temperature range.

INDUSTRIAL APPLICABILITY

Using the nonaqueous electrolytic solution of the present invention provides energy storage devices excellent in elec-

The invention claimed is:
1. A nonaqueous electrolytic solution, comprising: an electrolyte salt dissolved in a nonaqueous solvent; and a cyclic sulfonic acid ester compound of formula (I):

$$\text{(I)}$$

wherein
$R^1$ and $R^2$ each independently represents a hydrogen atom; an alkyl group comprising from 1 to 6 carbon atoms wherein at least one hydrogen atom is optionally substituted with a halogen atom, or a halogen atom;
L represents a divalent hydrocarbon group of an alkylene group comprising 2 or 3 carbon atoms wherein at least one hydrogen atom is substituted with $OR^3$, or a divalent hydrocarbon group of an alkylene group comprising 2 or 3 carbon atoms wherein at least one methylene ($CH_2$) group is substituted with a group $C(=O)$, and L is optionally substituted with an alkyl group comprising from 1 to 6 carbon atoms, a haloalkyl group comprising from 1 to 6 carbon atoms or a halogen atom;
$R^3$ represents a formyl group, an alkylcarbonyl group comprising from 2 to 7 carbon atoms, an alkenylcarbonyl group comprising from 3 to 7 carbon atoms, an alkynylcarbonyl group comprising from 3 to 7 carbon atoms, an alkoxycarbonyl group comprising from 2 to 7 carbon atoms, an alkenyloxycarbonyl group comprising from 3 to 7 carbon atoms, an alkynyloxycarbonyl group comprising from 4 to 7 carbon atoms, a dialkoxyphosphoryl group comprising from 2 to 12 carbon atoms, a group or a group —C(O)CH$_2$P(O)(OR$^5$)$_2$, and at least one hydrogen atom in R$^3$ is optionally substituted with a halogen atom;

R$^4$ represents an alkyl group comprising from 1 to 6 carbon atoms, a 2,2-dioxide-1,2-oxathiolan-4-yl group, or a 2,2-dioxide-1,2-oxathian-4-yl group; and R$^5$ represents an alkyl group comprising from 1 to 6 carbon atoms;

wherein a content of the cyclic sulfonic acid ester compound of formula (I) is from 0.001% to 10% by mass.

2. The nonaqueous electrolytic solution according to claim 1, wherein the cyclic sulfonic acid ester compound of formula (I) is at least one selected from the group consisting of 2,2-dioxide-1,2-oxathiolan-4-yl formate, 2,2-dioxide-1,2-oxathiolan-4-yl acetate, 2,2-dioxide-1,2-dioxathiolan-4-yl propionate, 2,2-dioxide-1,2-oxathiolan-4-yl isobutyrate, 2,2-dioxide-1,2-oxathiolan-4-yl pivalate, 2,2-dioxide-1,2-oxathiolan-4-yl acrylate, 2,2-dioxide-2-oxathiolan-4-yl methacrylate, 2,2-dioxide-1,2-oxathian-4-yl acetate, 2,2-dioxide-1,2-oxathiolan-4-yl methyl carbonate, 2,2-dioxide-1,2-oxathiolan-4-yl ethyl carbonate, 2,2-dioxide-1,2-oxathiolan-4-yl isopropyl carbonate, tert-butyl 2,2-dioxide-1,2-oxathiolan-4-yl carbonate, 2,2-dioxide-1,2-oxathiolan-4-yl vinyl carbonate, 2,2-dioxide-1,2-oxathiolan-4-yl diethylphosphate, bis(2,2-dioxide-1,2-oxathiolan-4-yl) sulfite, 2,2-dioxide-1,2-oxathiolan-4-yl 2-(diethoxyphosphoryl)acetate, 1,2-oxathiolan-4-one 2,2-dioxide, 5-methyl-1,2-oxathiolan-4-one 2,2-dioxide, 5,5-dimethyl-1,2-oxathiolan-4-one 2,2-dioxide, and 6,6-dimethyl-1,2-oxathian-4-one 2,2-dioxide.

3. The nonaqueous electrolytic solution according to claim 1, wherein the nonaqueous solvent comprises a cyclic carbonate and a linear ester.

4. The nonaqueous electrolytic solution according to claim 3, wherein the cyclic carbonate is at least one selected from the group consisting of ethylene carbonate, propylene carbonate, 1,2-butylene carbonate, 2,3-butylene carbonate, 4-fluoro-1,3-dioxolan-2-one, trans or cis-4,5-difluoro-1,3-dioxolan-2-one, vinylene carbonate, and vinylethylene carbonate.

5. The nonaqueous electrolytic solution according to claim 3, wherein the linear ester is a methyl group-comprising linear ester.

6. The nonaqueous electrolytic solution according to claim 1, wherein the electrolyte salt comprises at least one selected from the group consisting of LiPF$_6$, LiPO$_2$F$_2$, Li$_2$PO$_3$F, LiBF$_4$, LiN(SO$_2$CF$_3$)$_2$, LiN(SO$_2$C$_2$F$_5$)$_2$, LiN(SO$_2$F)$_2$, lithium difluorobis[oxalate-O,O]phosphate, and lithium tetrafluoro[oxalate-O,O']phosphate.

7. The nonaqueous electrolytic solution according to claim 1, further comprising at least one compound selected from the group consisting of a nitrile, a cyclic or linear S=O group-comprising compound, and a triple bond-comprising compound.

8. The nonaqueous electrolytic solution according to claim 7, wherein the at least one compound is a nitrile which is at least one selected from the group consisting of succinonitrile, glutaronitrile, adiponitrile and pimelonitrile.

9. The nonaqueous electrolytic solution according to claim 7, wherein the at least one compound is a S=O group-comprising compound which is at least one selected from the group consisting of 1,3-propanesultone, 1,3-butanesultone, 1,4-butanesultone, 2,4-butanesultone, ethylene sulfite and 4-(methylsulfonylmethyl)-1,3,2-dioxathiolane-2-oxide.

10. The nonaqueous electrolytic solution according to claim 7, wherein the at least one compound is a triple bond-comprising compound which comprises at least one selected from the group consisting of 2-propynyl methyl carbonate, 2-propynyl methanesulfonate, di(2-propynyl)oxalate, and 2-butyne-1,4-diyl dimethanesulfonate.

11. An energy storage device, comprising:
a positive electrode,
a negative electrode, and
the nonaqueous electrolytic solution according to claim 1.

12. The energy storage device according to claim 11, wherein the positive electrode comprises a lithium complex oxide-comprising material, and
the negative electrode comprises a carbon material comprising a graphite-type crystal structure.

13. A cyclic sulfonic acid ester compound of formula (II):

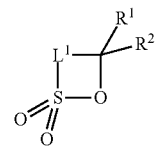

(II)

wherein

R$^1$ and R$^2$ each independently represent a hydrogen atom, an alkyl group comprising from 1 to 6 carbon atoms wherein at least one hydrogen atom is optionally substituted with a halogen atom, or a halogen atom;

L$^1$ represents a divalent hydrocarbon group of an alkylene group comprising 2 or 3 carbon atoms wherein at least one hydrogen atom is substituted with OR$^6$, or a divalent hydrocarbon group of an alkylene group comprising 3 carbon atoms wherein at least one methylene (CH$_2$) group is substituted with a group C(=O); L$^1$ is optionally substituted with an alkyl group comprising from 1 to 6 carbon atoms, a haloalkyl group comprising from 1 to 6 carbon atoms or a halogen atom; and when L1 is a divalent hydrocarbon group of an alkylene group comprising 3 carbon atoms wherein at least one methylene (CH$_2$) group is substituted with a group C(=O), R$^1$ and R$^2$ are hydrogen atoms;

R$^6$ represents a formyl group, an alkenylcarbonyl group comprising from 3 to 7 carbon atoms, an alkynylcarbonyl group comprising from 3 to 7 carbon atoms, an alkoxycarbonyl group comprising from 2 to 7 carbon atoms, an alkenyloxycarbonyl group comprising from 3 to 7 carbon atoms, an alkynyloxycarbonyl group comprising from 4 to 7 carbon atoms, a dialkoxyphosphoryl group comprising from 2 to 12 carbon atoms, a group —S(O)—OR$^4$ or a group —C(O)CH2P(O)(OR$^5$)$_2$, and at least one hydrogen atom in R$^6$ is optionally substituted with a halogen atom;

R$^4$ represents an alkyl group comprising from 1 to 6 carbon atoms, a 2,2-dioxide-1,2-oxathiolan-4-yl group, or a 2,2-dioxide-1,2-oxathian-4-yl group; and R$^5$ represents an alkyl group comprising from 1 to 6 carbon atoms;

wherein a content of the cyclic sulfonic acid ester compound of formula (II) is from 0.001% to 10% by mass.

14. The energy storage device according to claim 11, wherein L in the formula (I) represents the divalent hydrocarbon group of the alkylene group comprising 2 or 3 carbon atoms wherein at least one hydrogen atom is substituted with $OR^3$.

15. The energy storage device according to claim 11, wherein the nonaqueous electrolytic solution comprises the cyclic sulfonic acid ester compound of formula (I) in an amount of 0.05 to 5% by mass of the nonaqueous electrolytic solution.

16. The energy storage device according to claim 14, wherein the nonaqueous electrolytic solution comprises the cyclic sulfonic acid ester compound of formula (I) in an amount of 0.2 to 2% by mass of the nonaqueous electrolytic solution.

17. The nonaqueous electrolytic solution according to claim 1, wherein the cyclic sulfonic acid ester compound of formula (I) is included in an amount of from 0.05 to 8% by mass.

18. The nonaqueous electrolytic solution according to claim 17, wherein L in the formula (I) represents the divalent hydrocarbon group of the alkylene group comprising 2 or 3 carbon atoms wherein at least one hydrogen atom is substituted with $OR^3$.

\* \* \* \* \*